(12) United States Patent
Graham et al.

(10) Patent No.: US 10,716,470 B2
(45) Date of Patent: Jul. 21, 2020

(54) UNREVERSED PRISM GONIOSCOPY LENS

(71) Applicant: Ocular Instruments, Inc., Bellevue, WA (US)

(72) Inventors: Raymond D. Graham, Renton, WA (US); Peter G. Harrington, Sequim, WA (US)

(73) Assignee: OCULAR INSTRUMENTS, INC., Bellevue, WA (US)

( * ) Notice: Subject to any disclaimer, the term of this patent is extended or adjusted under 35 U.S.C. 154(b) by 0 days.

(21) Appl. No.: 15/953,212

(22) Filed: Apr. 13, 2018

(65) Prior Publication Data

US 2018/0271366 A1    Sep. 27, 2018

Related U.S. Application Data

(63) Continuation of application No. 14/703,707, filed on May 4, 2015, now abandoned.

(60) Provisional application No. 62/012,189, filed on Jun. 13, 2014, provisional application No. 61/987,678, filed on May 2, 2014.

(51) Int. Cl.
*A61B 3/117* (2006.01)
*A61B 3/125* (2006.01)
*G02B 17/08* (2006.01)

(52) U.S. Cl.
CPC ............. *A61B 3/117* (2013.01); *A61B 3/125* (2013.01); *G02B 17/086* (2013.01)

(58) Field of Classification Search
CPC ..... A61B 3/117; A61B 3/1173; A61B 3/1176; A61B 3/125; A61B 3/1208; G02B 17/086
USPC .................................................. 351/219, 220
See application file for complete search history.

(56) References Cited

U.S. PATENT DOCUMENTS

| 4,439,026 A | 3/1984 | Wilms |
| 5,309,187 A | 5/1994 | Crossman et al. |
| 5,523,810 A | 6/1996 | Volk |

(Continued)

FOREIGN PATENT DOCUMENTS

EP    1 889 566 A1    2/2008

OTHER PUBLICATIONS

International Preliminary Report on Patentability dated Nov. 17, 2016, issued in corresponding International Application No. PCT/US2015/029094, filed May 4, 2015, 1 page.

(Continued)

*Primary Examiner* — Jordan M Schwartz
(74) *Attorney, Agent, or Firm* — Christensen O'Connor Johnson Kindness PLLC

(57) ABSTRACT

In one embodiment, a double-reflecting contact lens for viewing the anterior chamber and the anterior chamber angle of an eye, the eye having an optical axis, includes a lens body having a contact end defining at least a portion of a first surface for contacting an eye and a viewing end defining at least a portion of a second surface, a first reflecting surface disposed adjacent the lens body, wherein the first reflecting surface is a planar surface extending from the viewing end to a middle region in the body between the viewing end and the contact end, and a second reflecting surface disposed adjacent the lens body, wherein the second reflecting surface is a planar surface extending from the viewing end to the contact end, the second reflecting surface opposing the first reflecting surface at an angle relative to the first reflecting surface.

11 Claims, 27 Drawing Sheets

(56) References Cited

U.S. PATENT DOCUMENTS

| | | | |
|---|---|---|---|
| 6,120,147 | A | 9/2000 | Vijfvinkel et al. |
| 6,976,758 | B2 | 12/2005 | Khaw et al. |
| 7,419,262 | B2 | 9/2008 | Whalen |
| 7,766,480 | B1 | 8/2010 | Graham et al. |
| 8,070,290 | B2 | 12/2011 | Gille et al. |
| 2004/0041979 | A1 | 3/2004 | Erickson et al. |
| 2004/0196434 | A1 | 10/2004 | Khaw et al. |
| 2005/0288745 | A1 | 12/2005 | Andersen et al. |
| 2008/0043199 | A1 | 2/2008 | Whalen |
| 2009/0185135 | A1* | 7/2009 | Volk .................. G02B 17/0808 351/219 |
| 2010/0134759 | A1 | 6/2010 | Silvestrini et al. |
| 2010/0265461 | A1 | 10/2010 | Gille et al. |
| 2012/0113392 | A1* | 5/2012 | Heacock ................ A61B 3/117 351/219 |
| 2013/0103145 | A1 | 4/2013 | John et al. |

OTHER PUBLICATIONS

International Search Report dated Aug. 26, 2015, issued in corresponding International Application No. PCT/US2015/029094, filed May 4, 2015, 4 pages.

Written Opinion of the International Searching Authority dated Aug. 26, 2015, issued in corresponding International Application No. PCT/US2015/029094, filed May 4, 2015, 10 pages.

Ocular Mori Upright Surgical Gonio Lens; Ocular Instruments Catalogue 2012, p. 51.

Tano Double Mirror Surgical Gonio Lens; Ocular Instruments Catalogue 1997, p. 23.

* cited by examiner

MICROSCOPE 16X, LENS 1.3X

MICROSCOPE 25X, LENS 0.8X

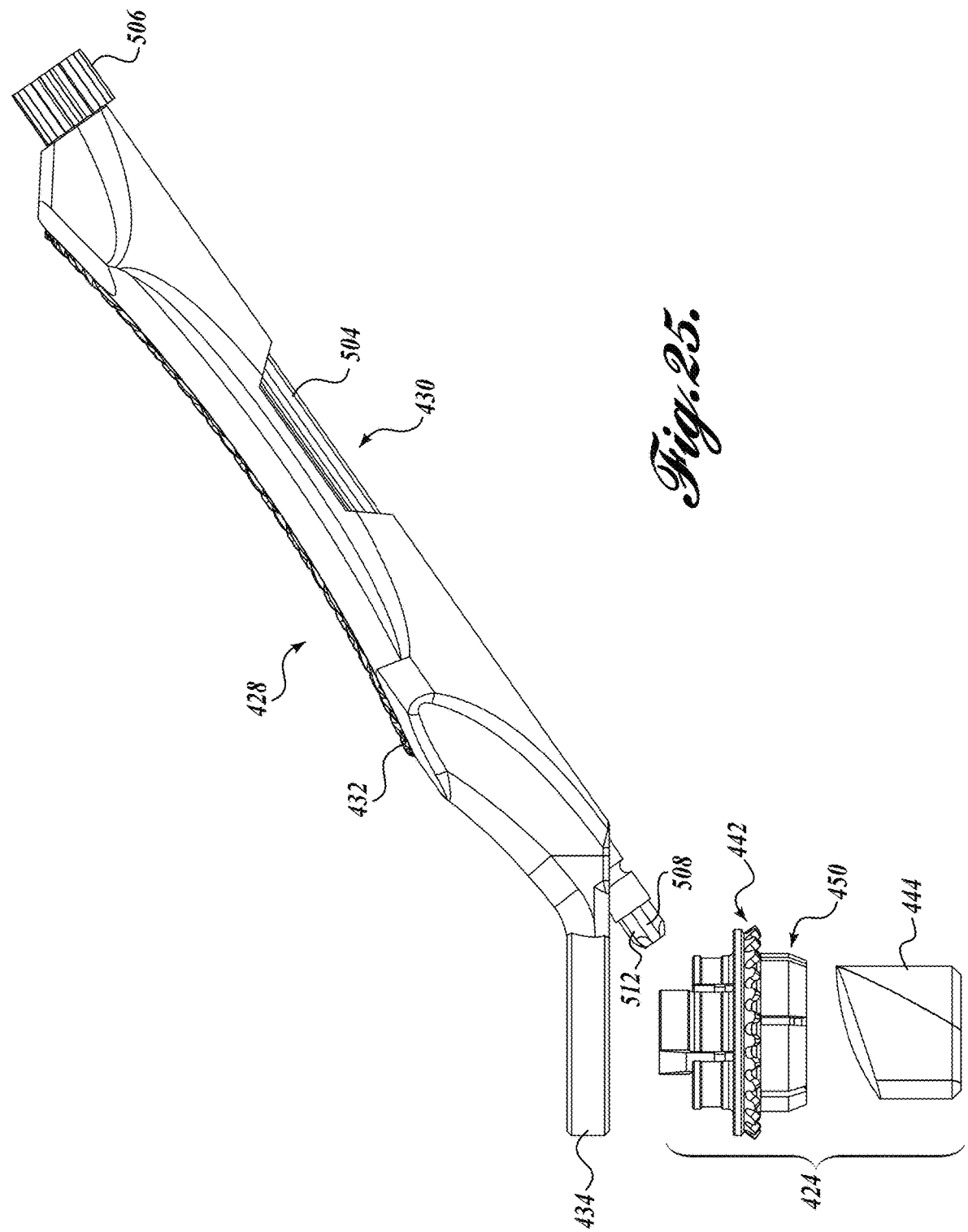

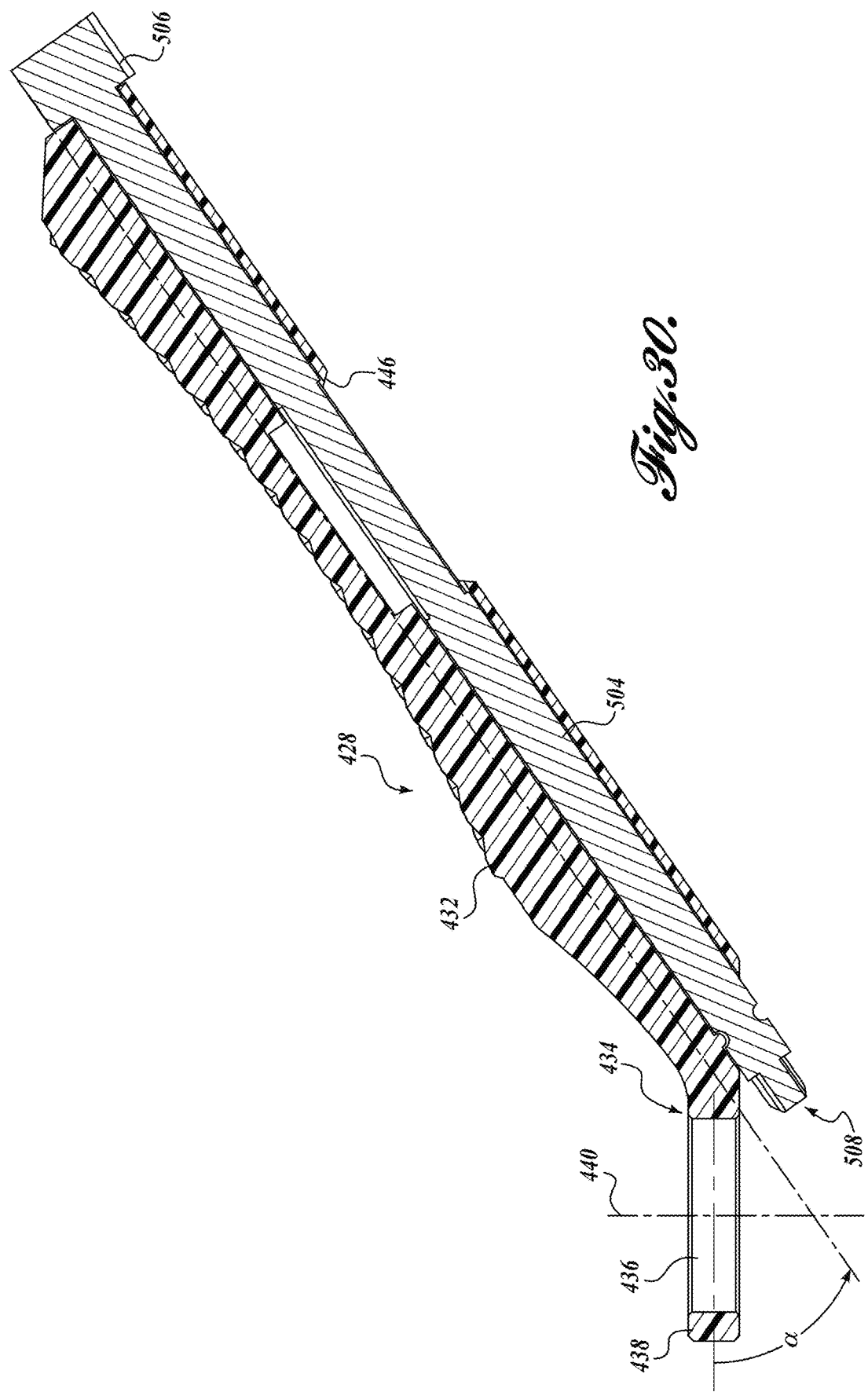

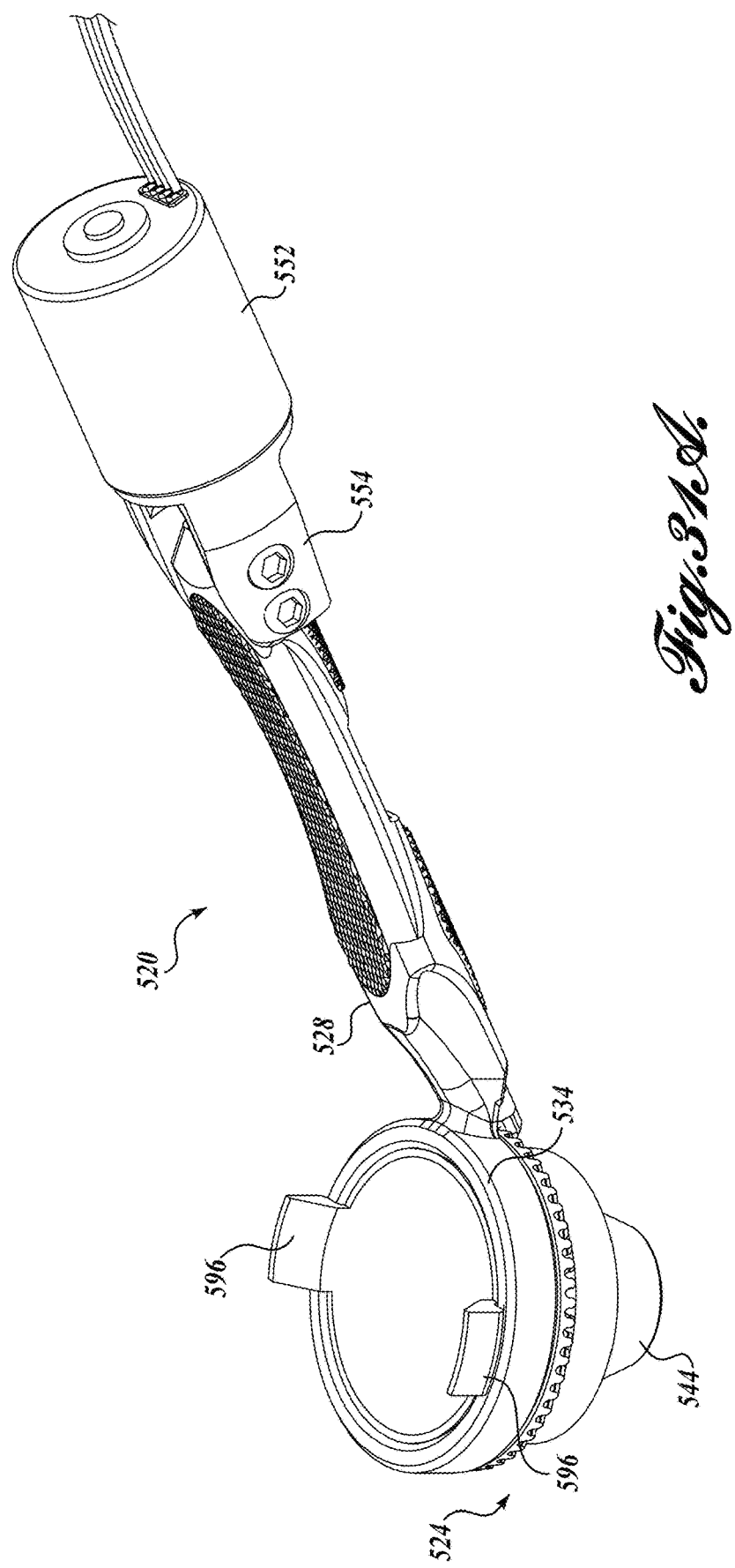

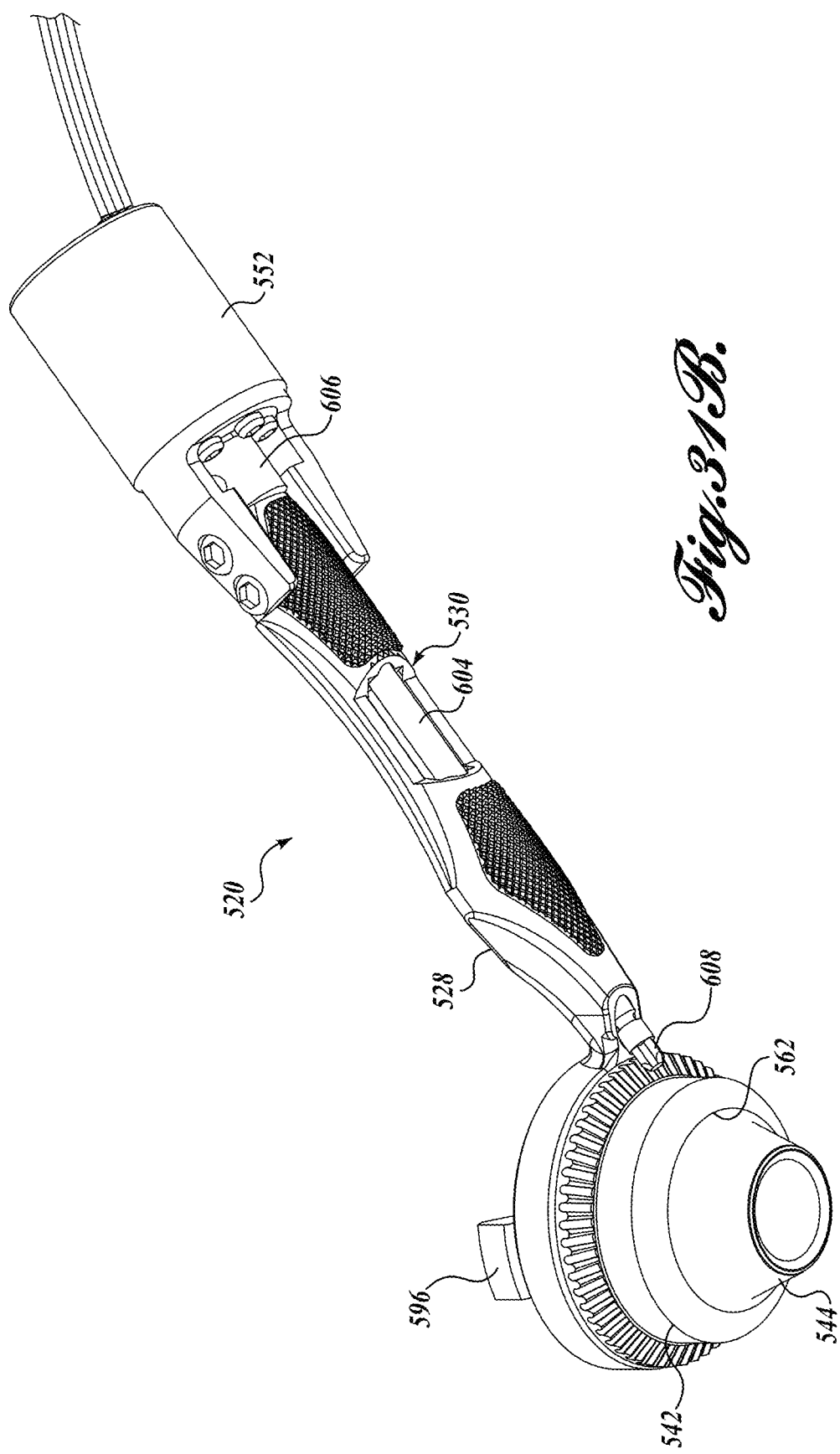

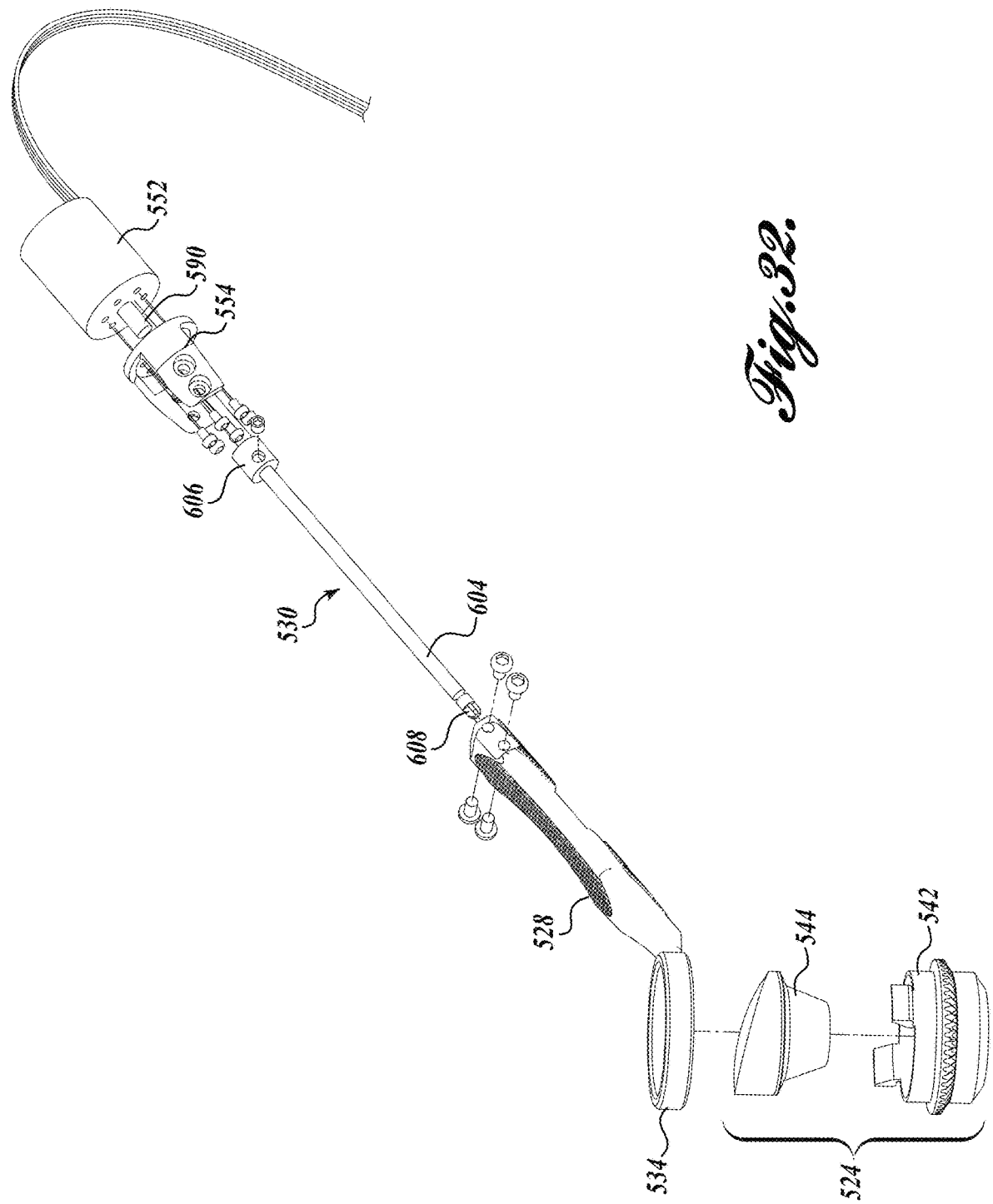

UNREVERSED PRISM GONIOSCOPY LENS

CROSS-REFERENCES TO RELATED APPLICATIONS

This application is a continuation of U.S. patent application Ser. No. 14/703,707, filed May 4, 2015, which claims the benefit of U.S. Provisional Application No. 62/012,189, filed Jun. 13, 2014, and U.S. Provisional Application No. 61/987,678, filed May 2, 2014, the disclosures of which are hereby expressly incorporated by reference herein in their entireties.

BACKGROUND

In some ophthalmic procedures, it is desirable to view the periphery of the anterior chamber and anterior chamber angle of a patient's eye when the doctor's line of sight is along the optical axis of the eye. Having a line of sight along the optical axis of the eye is not possible with previously designed lenses. Therefore, there exists a need for a lens assembly enabling such a view for various ophthalmic procedures.

SUMMARY

This summary is provided to introduce a selection of concepts in a simplified form that are further described below in the Detailed Description. This summary is not intended to identify key features of the claimed subject matter, nor is this summary intended to be used as an aid in determining the scope of the claimed subject matter.

The present disclosure relates generally to instruments of the type broadly applicable to ophthalmic procedures. As will be described in more detail below, the one or more examples of instruments includes a contact lens configured for direct contact for viewing parts of an eye.

In accordance with one embodiment of the present disclosure, a double-reflecting contact lens for viewing the anterior chamber and the anterior chamber angle of an eye, the eye having an optical axis, is provided. The lens includes: (a) a lens body having a contact end defining at least a portion of a first surface for contacting an eye and a viewing end defining at least a portion of a second surface; (b) a first reflecting surface disposed adjacent the lens body, wherein the first reflecting surface is a planar surface extending from the viewing end to a middle region in the body between the viewing end and the contact end; and (c) a second reflecting surface disposed adjacent the lens body, wherein the second reflecting surface is a planar surface extending from the viewing end to the contact end, the second reflecting surface opposing the first reflecting surface at an angle relative to the first reflecting surface.

In accordance with another embodiment of the present disclosure, a method of viewing the anterior chamber and the anterior chamber angle of an eye, the eye having an optical axis, is provided. The method includes: (a) placing a double-reflecting contact lens on the eye of a patient, the lens having a lens body, a first reflecting surface disposed adjacent the lens body, wherein the first reflecting surface is a planar surface extending from the viewing end to a middle region in the body between the viewing end and the contact end, and a second reflecting surface disposed adjacent the lens body, wherein the second reflecting surface is a planar surface extending from the viewing end to the contact end, the second reflecting surface opposing the first reflecting surface at an angle relative to the first reflecting surface; (b) holding the contact lens in a substantially constant position and viewing a first location in the anterior chamber of the eye of the patient; and (c) rotating the contact lens on the eye of the patient and viewing a second location in the anterior chamber of the eye of the patient.

In any of the embodiments described herein, the second reflecting surface may be parallel to the optical axis of the eye.

In any of the embodiments described herein, the second reflecting surface may be a planar reflecting surface extending from the contact end to the viewing end of the lens.

In any of the embodiments described herein, the first reflecting surface may be at an angle relative to the optical axis of the eye.

In any of the embodiments described herein, the first reflecting surface may be a planar reflecting surface extending for a least a portion of the distance between the contact end and the viewing end of the lens, wherein the first reflecting surface opposes the second reflecting surface at an angle relative to the second reflecting surface.

In any of the embodiments described herein, the first reflecting surface may extend from a first end at the viewing end of the lens to a second end in a middle region in the body between the viewing end and the contact end.

In any of the embodiments described herein, the first reflecting surface may be truncated at a middle region in the body between the viewing end and the contact end.

In any of the embodiments described herein, the lens body may have an outer surface different from the contact end and the viewing end.

In any of the embodiments described herein, the lens body may extend between the planar shelf of the first reflecting surface and the contact end of the lens.

In any of the embodiments described herein, a planar shelf may adjoin the first reflecting surface, wherein the planar shelf extends from the second end of the first planar reflecting portion to the outer surface of the body.

In any of the embodiments described herein, the planar shelf adjoining the first reflecting surface may be perpendicular to the first planar reflecting portion of the first reflecting surface.

In any of the embodiments described herein, the lens may further include a first outer portion of the lens adjacent the first reflecting surface and the planar shelf portion.

In any of the embodiments described herein, wherein the first outer portion may be defined by at least the first reflecting surface, the planar shelf, and an outer surface of the first outer portion.

In any of the embodiments described herein, the lens may further include a second outer portion of the lens adjacent the second reflecting surface.

In any of the embodiments described herein, the second outer portion may be defined by at least the second reflecting surface and an outer surface on the second outer portion.

In any of the embodiments described herein, wherein the lens body may be a prism having a magnification in the range of greater than 1× to about 2×.

DESCRIPTION OF THE DRAWINGS

The foregoing aspects and many of the attendant advantages of this disclosure will become more readily appreciated by reference to the following detailed description, when taken in conjunction with the accompanying drawings, wherein:

FIGS. 24A-36 are views of embodiments of lens handles for rotational control of the lenses.

DETAILED DESCRIPTION

Embodiments of the present disclosure are generally directed to contact lenses for use in ophthalmic procedures. Referring to FIGS. 1-7, a contact lens assembly 20 in accordance with one embodiment of the present disclosure is a lens designed for direct contact with the cornea C of an eye E (see FIG. 1). The lens assembly 20 is unreversed prism gonioscopy lens assembly designed to view the periphery of the anterior chamber angle A of the eye E. In that regard, the lens assembly 20 of the illustrated embodiment is a two-mirrored lens for an unreversed view.

Figure 15:
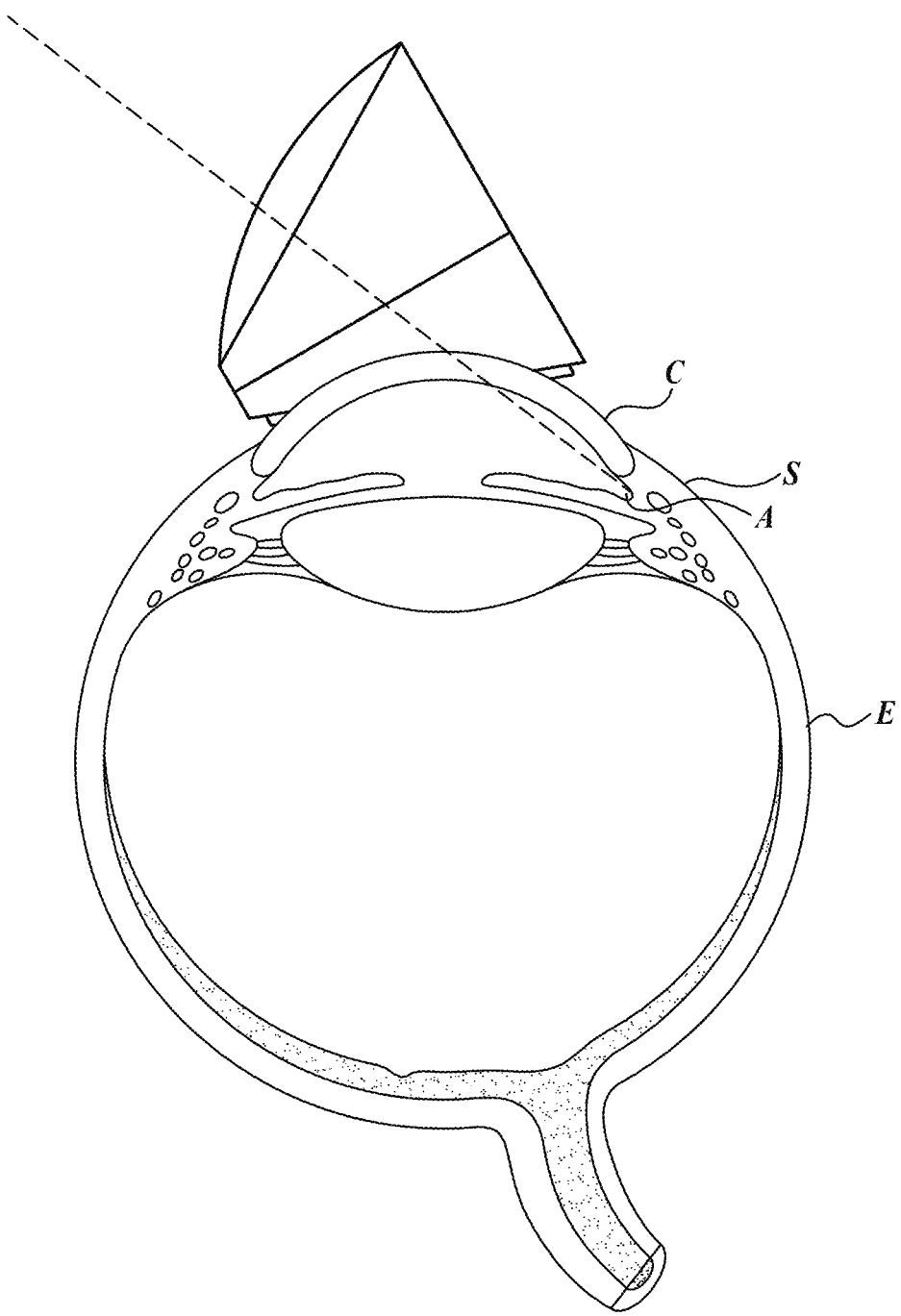
FIG. 15 is a side cross-sectional view of a previously designed Swan-Jacob Gonioprism contact lens.

Common lenses for use in gonioscopy (i.e., viewing the anterior chamber angle of the eye) are known as meniscus gonioscopy lenses, such as the commercially available Swan-Jacob Gonioprism Lens (the "Swan lens") by Ocular Instruments, Inc. (see FIG. 15). The Swan lens is a contact lens having a contact surface that conforms to the surface of an eye. The contact surface is curved and has an optical axis that may be aligned with the optical axis of the eye. The Swan lens also has a viewing surface that is offset in an anterior direction from the contact surface and has an optical axis that intersects the optical axis of the contact surface. When the Swan lens is positioned on the eye, the user may view the anterior chamber angle of the eye by looking into the Swan lens along an axis that crosses the contact surface optical axis.

Embodiments of the present disclosure are directed to unreversed prism gonioscopy lens assemblies that allow for visualization of the anterior chamber angle A of the eye. The visualization is substantially normal to the surgical field, but not normal to an anterior curve that is offset at an angle relative to the patient's eye, as in typical Swan lenses. In that regard, the direction of observation, which may be through a microscope, is substantially parallel to the optical axis 40 of the patient's eye E. In accordance with embodiments of the present disclosure, substantially normal to the surgical field may include a range of up to + or −10 degrees from normal.

One advantage of such a normal viewing angle is that the doctor may remain in one position without adjusting a microscope if using one, while simply rotating the lens to view the entire 360 degrees of the anterior chamber of the patient's eye. For 360 degree rotation without adjusting the position of the lens assembly 20, the optical path P1 for viewing the anterior chamber angle A of the patient's eye E must be within a distance D from the optical axis 40 of the patient's eye E, wherein the distance D is less than one half of the greatest distance L across the anterior chamber (see FIG. 1).

Figure 16:
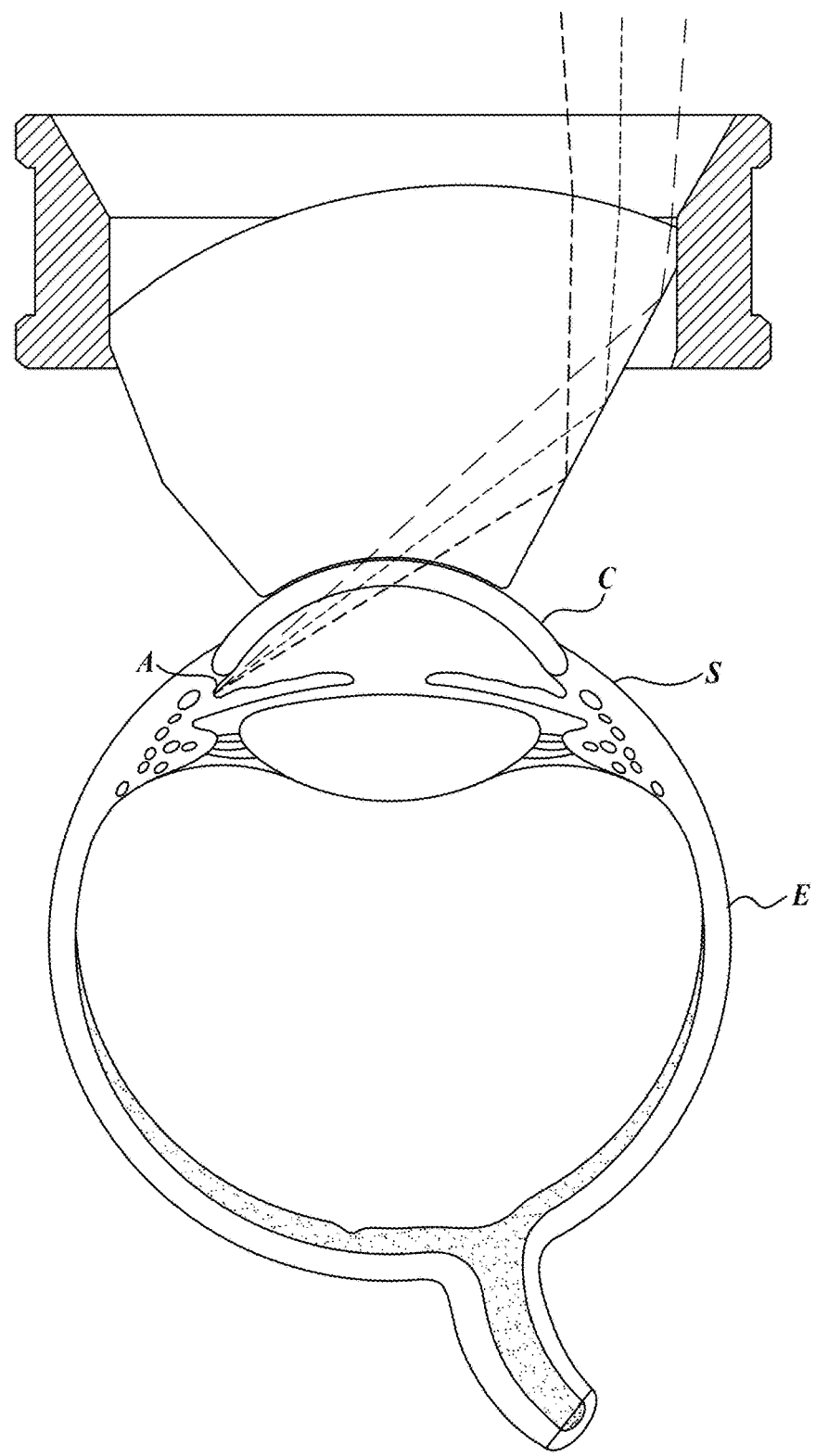
FIG. 16 is a side cross-sectional view of a previously designed Ahmed 1.5× Surgical Gonio contact lens.

An exemplary two-mirror unreversed lens assembly, although more difficult to build than a single-mirror lens assembly, allows the user to see the patient's eye in an unreversed view, as opposed to a reversed "mirror image" view seen by a single-mirror lens assembly. An exemplary single mirror lens assembly is the commercially available Ahmed 1.5× Surgical Gonio, by Ocular Instruments, Inc. (see FIG. 16). The single mirror in the Ahmed lens provides visualization substantially normal to the surgical field, but the user sees the patient's eye in a reversed view. In contrast to a single-mirror view, a two-mirror unreversed view is particularly helpful when performing surgery because the tactile movements of the instruments match what is seen in the unreversed image.

Referring to FIGS. 1-7, lens assembly 20 includes a lens body 22 having a contact end 24 defining at least a portion of a first surface or an eye contact surface 26 and a viewing end 28 defining at least a portion of a second surface or a viewing surface 30. The lens body 22 is a prism defining the viewing lens through which the user peers at the patient's eye E. The lens body 22 may be manufactured from glass, acrylic, or any other material having suitable optics and capable of being cleaned and/or sterilized.

The eye contact surface 26 is designed and configured for contact with the cornea region C of an eye E. Therefore, the eye contact surface 26 is concave in shape and conforms to and is compatible with the convex anterior surface of an eye E. In the illustrated embodiment, the radius of curvature of the eye contact surface 26 is about 7.85 mm; however, other radii of curvatures designed to approximate the curvature of an average human eye (or animal eye in veterinary applications) are within the scope of the present disclosure. For example, the radius of curvature of the eye contact surface 26 may be in the range of about 6.5 mm to about 9 mm.

In one embodiment of the present disclosure, the lens assembly 20 may be sized to have a contact surface 26 diameter in the range of less than about 10 mm. In that regard, the lens assembly 20 is compatible with the average cornea, wherein the circular region where the cornea C meet the sclera S has a diameter of about 12 mm. In one embodiment of the present disclosure, the contact surface 26 diameter may be about 9.75 mm. Optical axis 40 extends through the eye contact surface 26. The contact surface allows for a clear corneal incision, for example at a point of incision I in FIG. 1 such that a surgical tool (not shown) can be used in the anterior chamber angle A opposite the point of incision I.

The viewing surface 30 may be a curved surface and its optical axis may intersect the eye's optical axis 40. In the illustrated embodiment, the radius of curvature of the viewing surface 30 is about 20 mm; however, other viewing surface 30 curvatures are within the scope of the present disclosure. The viewing surface 30 curvature can provide image magnification through the lens body 22. Laterally shifting and/or tilting the viewing surface 30 can enhance the image quality.

The use of prism (reflecting) surfaces 50 and 52 in the lens assembly 20 allows for viewing the anterior chamber angle A while allowing the user to view from a view angle substantially parallel to the optical axis 40 of the eye E (as opposed to a more tilted view angle). As mentioned above, such a view angle may be along the optical axis 40, substantially parallel to the optical axis 40, or within an angle range of up to + or −10 degrees of parallel to the optical axis 40. Such a view angle provides the advantage of allowing the user to view multiple areas around the anterior chamber angle A the eye E without needing to adjust his or her body and/or the angle of the microscope relative to the patient.

As mentioned above, the lens assembly 20 of the illustrated embodiment is an unreversed prism gonioscopy contact lens assembly. In that regard, the lens assembly 20 includes a first reflecting surface 50 disposed adjacent the lens body 22. In the illustrated embodiment, the first reflecting surface 50 is substantially planar and intersects the contact and viewing ends 24 and 28 of the lens body 22. The lens assembly 20 further includes a second reflecting surface 52 disposed adjacent the lens body 22 opposing the first reflecting surface 50, wherein the second reflecting surface 52 is substantially planar and intersects the contact and viewing ends 24 and 28 of the lens body 22.

The reflecting surfaces 50 and 52 may be total internal reflecting (TIR) surfaces or coated with appropriated surfaces to provide mirrored surfaces. In some embodiments, reflecting surface 50 may be a TIR surface next to air. In some embodiments, reflecting surface 52 may be a mirrored surface due to the typical angle of incidence.

In the illustrated embodiment, the first and second reflecting surfaces 50 and 52 are substantially planar. However, non-planar surfaces are also within the scope of the present disclosure. In that regard, the surfaces 50 and 52 may be designed with some curvature to correct the image or add magnification to the view. Although non-planar surfaces may add magnification, they also may distort the image.

In the illustrated embodiment, the first reflecting surface 50 is positioned at an angle of about 30 degrees relative to the optical axis 40 and intersects the optical axis 40 near the eye contact surface 26. In some embodiments of the present disclosure, the first reflecting surface 50 may be positioned at an angle in the range of about 22 to about 38 degrees relative to the optical axis 40, or in the range of about 25 to about 35 degrees relative to the optical axis 40.

The second reflecting surface 52 is positioned substantially parallel to the optical axis 40. In some embodiments of the present disclosure, the second reflecting surface 52 may be positioned at an angle in the range of about 85 to about 95 degrees+/−5 degrees relative to the optical axis 40. In this configuration, the viewer views the anterior chamber angle A of the eye E along path P1. Likewise, the viewer may also view the anterior chamber angle A of the eye E from a slightly tilted view along one of paths P2 or P3.

As seen in the illustrated embodiment of FIGS. 1-7, the lens assembly 20 may have a circular cross-section through a plane perpendicular to the optical axis 40. To make a circular cross-section, the lens assembly 20 may include optional first and second outer portions 70 and 80, such as glass filler portions, as can be seen in exploded view in FIG. 7. In other embodiments of the present disclosure, either of first and second outer portions 70 and 80 or both may not be included in the lens assembly 20.

The first outer portion 70 is attached to the first reflecting surface 50 on the opposite side of the first reflecting surface 50. The first outer portion 70 may include a contact end 72 defining at least a portion of the eye contact surface 26 and viewing end 74 defining at least a portion of the viewing surface 30. First outer portion 70 is not needed optically, but is designed to protect first reflecting surface 50 and to provide a lens assembly 20 having a circular cross-section through a plane perpendicular to the optical axis 40.

The second outer portion 80 is attached to the second reflecting surface 52 on the opposite side of the second reflecting surface 52. The second outer portion 80 may include a contact end 82 defining at least a portion of the eye contact surface 26 and viewing end 84 defining at least a portion of the viewing surface 30. Second outer portion 80, like first outer portion 70, is not needed optically, but is designed to protect second reflecting surface 52 and to provide a lens assembly 20 having a circular cross-section through a plane perpendicular to the optical axis 40.

In the illustrated embodiment, the first and second outer portions 70 and 80 are shown as extending between and defining a portion of the eye contact and viewing surfaces 26 and 30 of the lens assembly 20. However, in certain embodiments, the first and second outer portions 70 and 80 need not extend completely from the eye contact surface 26 to the viewing surface 30 of the lens assembly 20. In that regard, these portions 70 and 80 may extend a portion of the distance between the eye contact surface 26 and the viewing surface 30 of the lens assembly 20. (See, for example, the alternate embodiment of FIGS. 8-14.)

Figure 19:
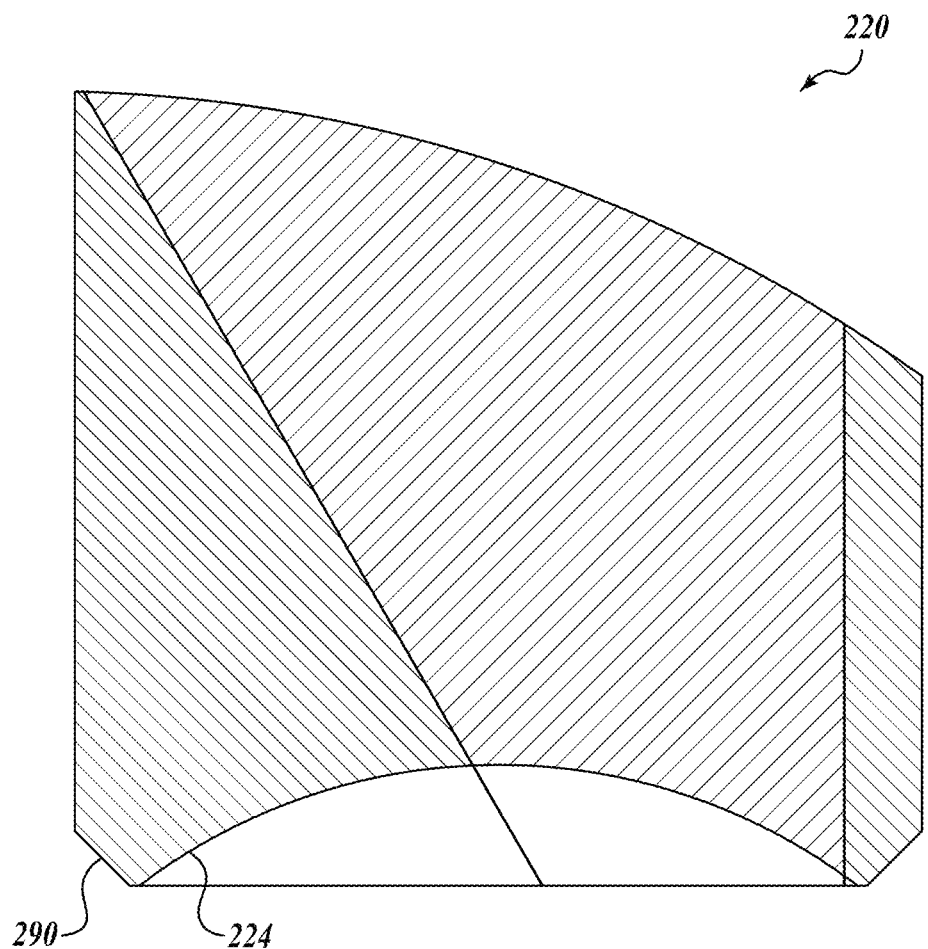
FIGS. 19 and 20 are views of a contact lens assembly in accordance with another embodiment of the present disclosure, with the contact lens assembly including a beveled edge.
Figure 20:
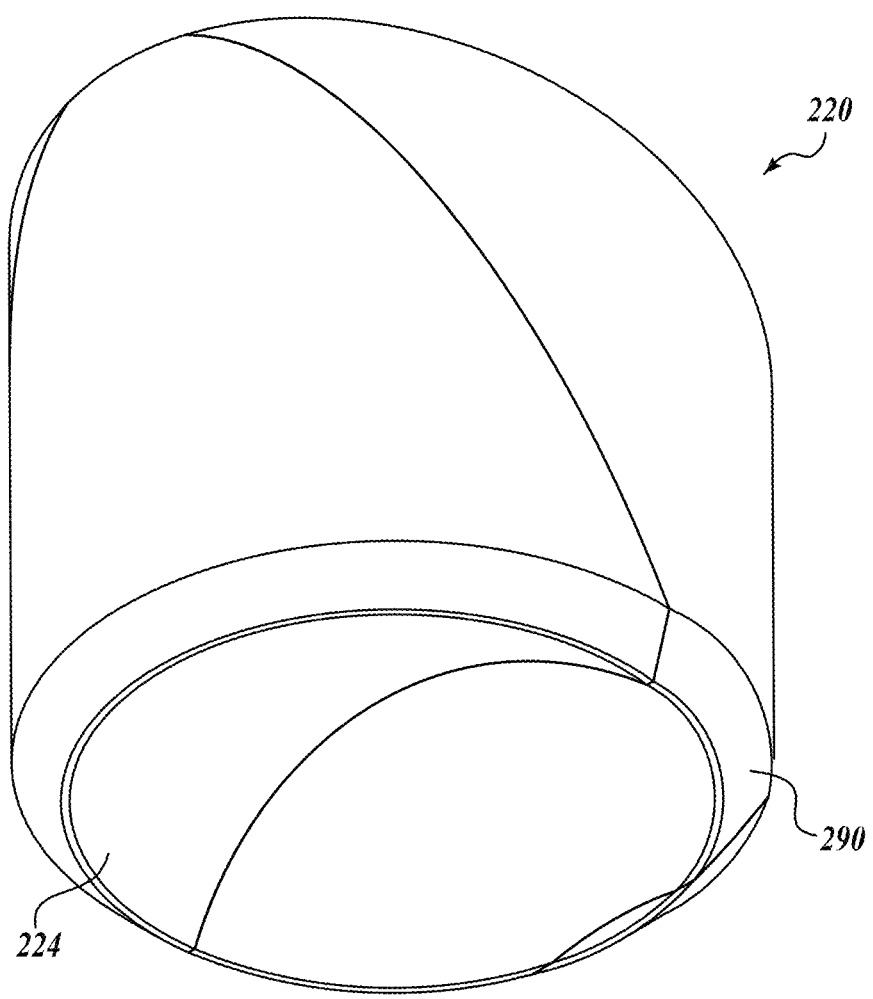

Referring to FIGS. 19 and 20, in one embodiment of the present disclosure, the contact end 224 includes an optional beveled edge 290 at the contact end 224 of the lens assembly 220. The beveled edge 290 allows for reduced contact area of the lens assembly 220 with the eye E (as compared to the viewing cross-sectional area of the lens assembly) to enable the use of surgical instruments on the eye E in or near the outer circumference of the beveled edge 290. In that regard, there is reduced interference around the eye E for the user who may be performing surgery on the eye E while using the contact lens assembly 220. In the illustrated embodiment, the bevel 90 is at a 45 degree angle relative to the optical axis. However, other angles for the bevel 290 are also within the scope of the present disclosure.

In addition to or in lieu of a bevel, exclusion of one or both of the first and second outer portions 70 and 80 (see FIG. 1) may also provide reduced interference around the eye E for the user who may be performing surgery on the eye E while using the contact lens assembly 20.

The lens body 22 is designed and configured to include magnification to aid in visualization of the anterior chamber angle A of the eye E. Magnification is typically provided by use of an external microscope. However, high magnification in an external microscope can decrease the field of view seen by the microscope, limiting the view outside the ophthalmic contact lens. For example, compare the field of view in FIG. 18A for a previously designed lens designed for vitrectomy viewing and having no magnification and FIG. 18B for a lens assembly in accordance with embodiments of the present disclosure including 1.3× magnification.

Figure 17:
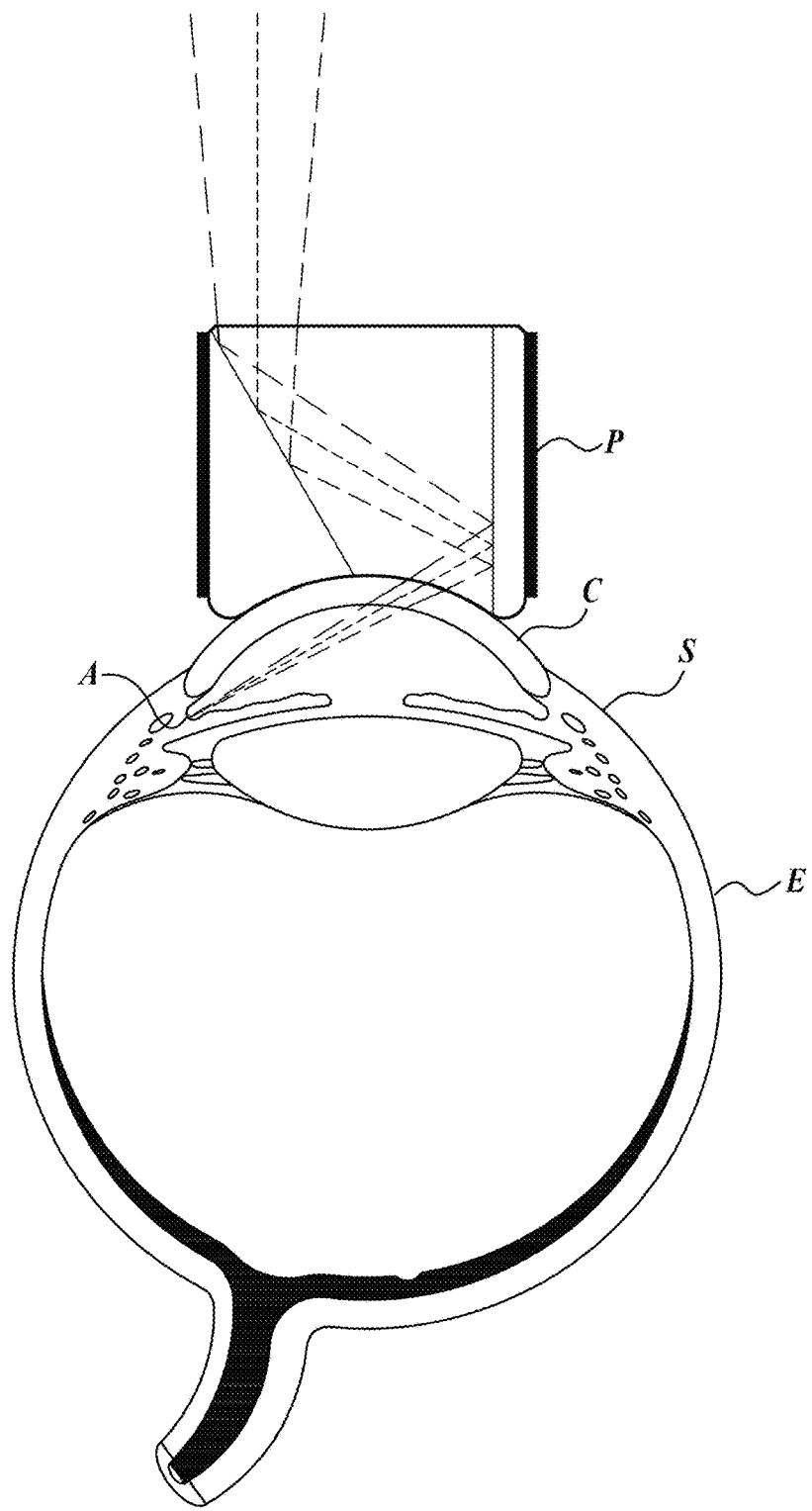
FIG. 17 is a side cross-sectional view of a previously designed Tano contact lens.
Figure 18B:
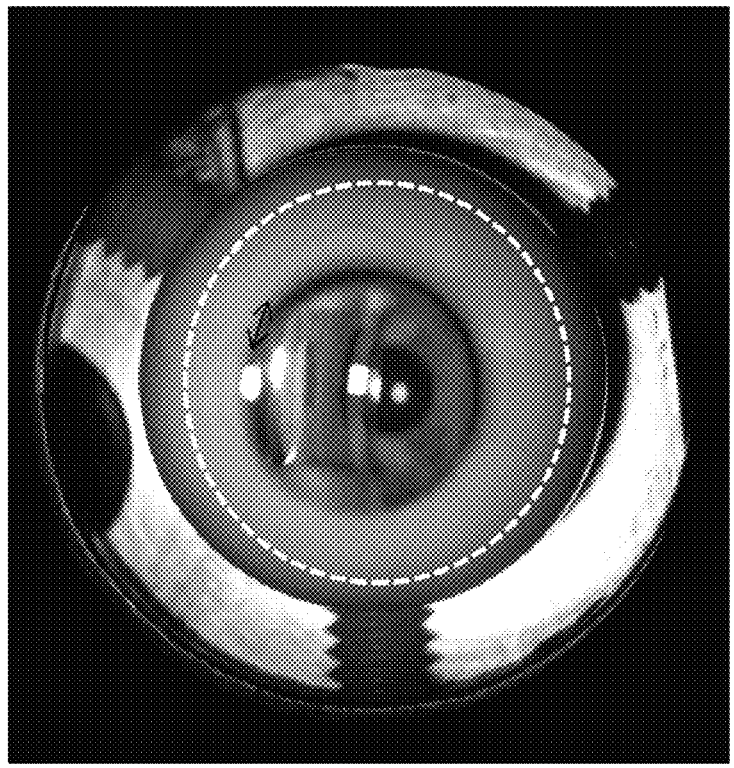
FIGS. 18A and 18B are comparative microscope views showing the field of view with a previously designed Tano contact lens and a contact lens assembly in accordance with one embodiment of the present disclosure.
Figure 18A:
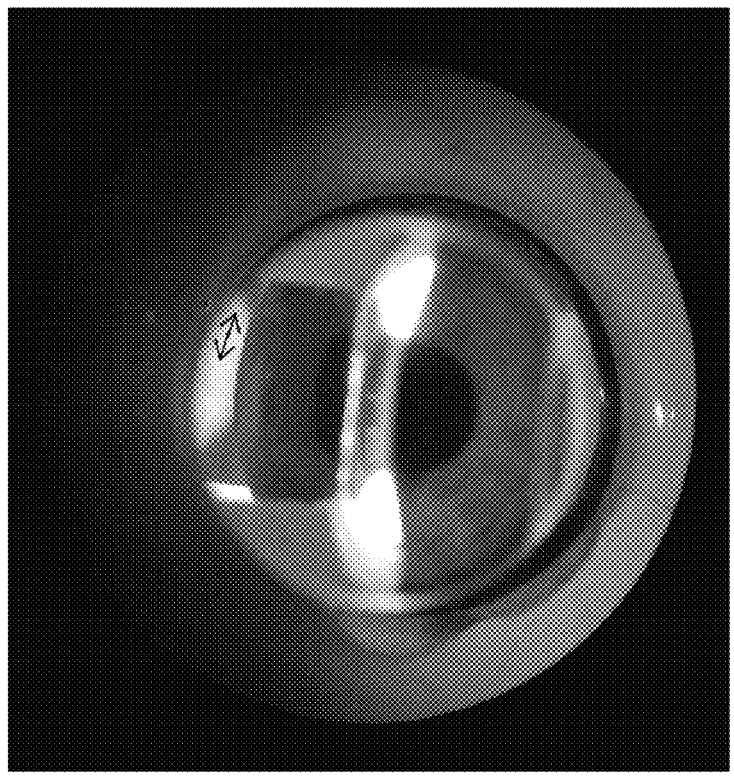

In FIG. 18A, a photograph of an eye is shown at a microscope setting of 25× using the Tano Lens (the "Tano lens") by Ocular Instruments, Inc., commercially available in 1997. The Tano lenses, one example of which is seen in FIG. 17, were developed for viewing the vitrectomy region in the back of the eye and/or the anterior chamber angle, but were not designed for surgical procedures in the anterior chamber angle A of the eye E. Referring to FIG. 17, the Tano lens is a double-mirror lens assembly having no curvature on its viewing end. Therefore, the magnification provided by the Tano lens is less than 1×, at about 0.8×. The previously designed Tano lens for viewing the anterior chamber angle did not have enough magnification for surgery. Its primary use was for inspection of the anterior chamber angle during vitrectomy surgery. Therefore, the diameter of the Tano lens was designed to fit into common vitrectomey rings that are sutured to the eye during surgery.

Because of limitations in manufacturing processes, reflective surfaces, and adhesives in the 1990s, the Tano lens was coated with an outer protective coating P to prevent degradation of the lens particularly at the seams. Such protective coatings did not impair light entry for viewing the vitrectomy region in the back of the eye. However, the inventors found such protective coatings to impair the surgical view of the anterior chamber angle. Therefore, embodiments of the present disclosure are manufactured with advanced manufacturing processes, reflective surfaces, and adhesives without requiring an outer protective coating.

Because of the reduced magnification in the Tano lens, high magnification of 25× is used in the microscope to adequately view the anterior chamber angle A of the eye E for surgery in the trabecular meshwork. The result of such high magnification in the microscope is a limited view of the surgical field, impairing the surgeon's ability to operate, as can be seen in FIG. 18A.

Referring now to FIG. 18B, a photograph of an eye is shown at a microscope setting of 16× using a lens assembly in accordance with embodiments of the present disclosure having 1.3× magnification in the lens assembly. With reduced microscope magnification of 16× (as compared to 25× in FIG. 18A), the anterior chamber angle A of the eye E can be adequately viewed while still provided a large view of the surgical field.

In accordance with embodiments of the present disclosure, magnification is provided in the lens body 22 itself to increase magnification of the eye E while maintaining the microscope field of view. Suitable magnification may be in the range of greater than 1×, in the range of about greater than 1× to 2×, in the range of about 1.1× to about 1.5×, or in the range of about 1.2× to about 1.3×.

The illustrated embodiment of FIGS. 1-7 may be useful in glaucoma examination and/or surgical procedures, for example, procedures for disorders such as open-angle and/or closed-angle glaucoma. Generally described, aqueous humor, a fluid that is produced within the eye, drains via the trabecular meshwork into the canal of Schlemm then into the scleral plexuses and into general blood circulation of the body.

The major risk factor for most glaucoma's, and the focus of treatment, is relieving increased intraocular pressure, which is a function of the production of liquid aqueous humor without adequate drainage. In open/wide-angle glaucoma, flow is reduced through the trabecular meshwork as a result of degeneration and/or obstruction of the trabecular meshwork. To relieve the increased intraocular pressure, one or more stents may be inserted into the trabecular meshwork in various locations.

For example, a stent for Micro Invasive Glaucoma Surgery (MIGS) has been recently approved by the FDA to improve fluid outflow in open-angle glaucoma patients for implantation in the patient's eye during cataract surgery In the cataract procedure, the microscope is generally positioned such that the doctor's line of sight is along the optical axis. Therefore, it is desirable to perform the anterior chamber angle procedures with the microscope in the same position. Embodiments of the present disclosure enable a view the periphery of the anterior chamber when the doctor's line of sight is along the optical axis.

Other procedures performed after a cataract surgery may include ab interno approaches include synechiolysis, goniotomy, placenent of aqueas drainage stents etc. In ab interno approaches, the trabecular meshwork is engaged from inside the anterior chamber, having the benefits of only clear cornea healing with the sclera and conjunctiva left intact.

To insert such stents during an open-angle glaucoma surgical procedure, the user may move or rotate the lens assembly 20 to a first position on the eye E to insert a first stent into the anterior chamber angle A of the eye E, then to a second position on the eye E to insert a second stent into another place in the anterior chamber angle A of the eye E. Likewise, during an examination procedure, the user may move the lens assembly 20 from a first position on the eye E to examine a first portion of the anterior chamber angle A, then to a second position on the eye E to examine a second portion of the anterior chamber angle A.

Embodiments of the present disclosure may also be used in closed-angle glaucoma surgical procedures. In closed-angle glaucoma (or angle closure glaucoma), the iridocorneal angle may become closed because of forward displacement of the iris against the cornea. Such displacement may impede aqueous fluid flow from the posterior chamber to the anterior chamber of the eye and then out of the trabecular network. This accumulation of aqueous humor causes an acute increase of pressure and pain.

To view areas of the eye where the anterior chamber angle is closed, embodiments of the present disclosure allow the user to rotate the lens to view multiple positions along the perimeter of the anterior chamber angle and, in some cases, the entire periphery of the anterior chamber angle.

Figure 1:
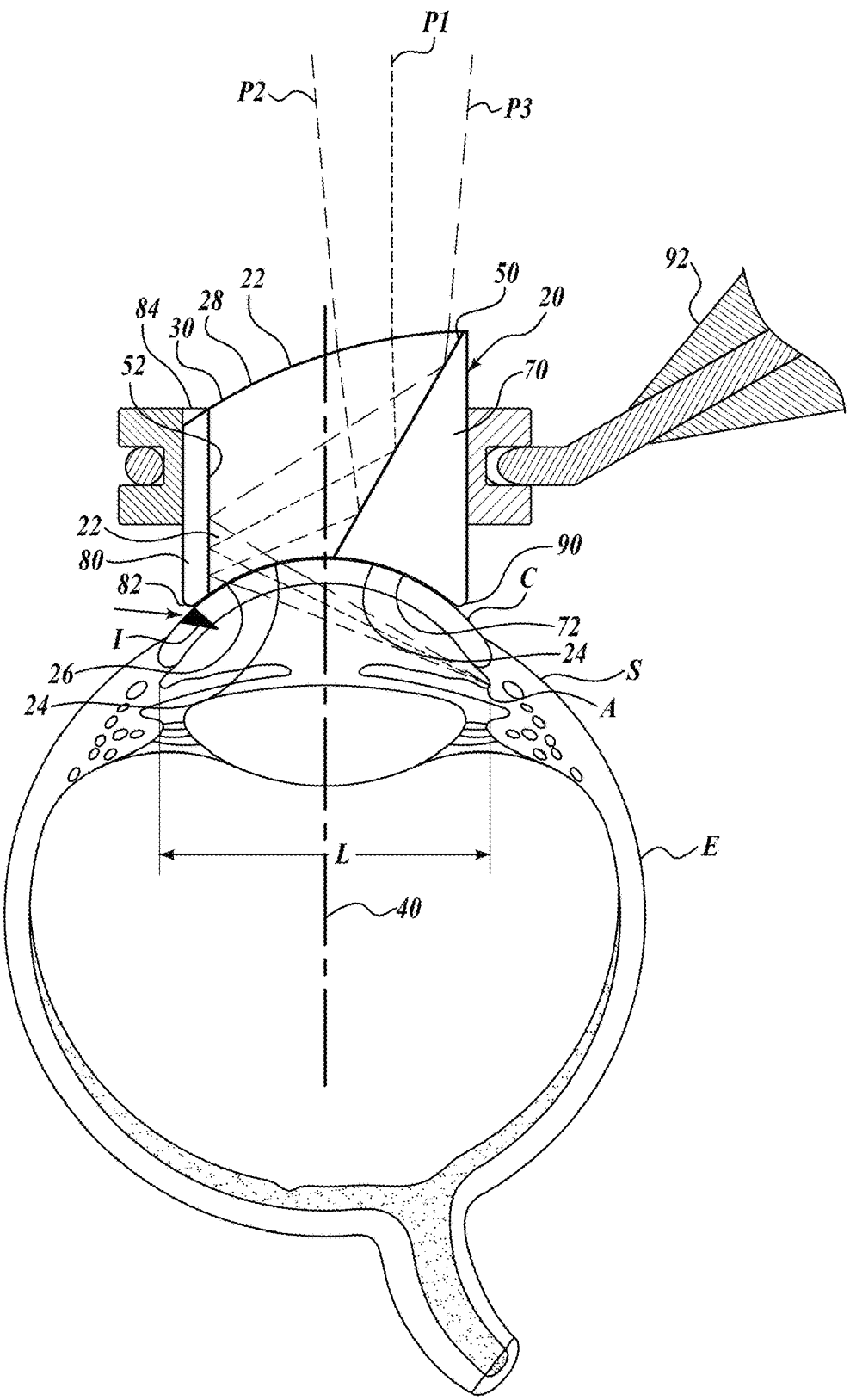
FIG. 1 is a side cross-sectional view of a contact lens assembly in contact with an eye in accordance with one embodiment of the present disclosure.
Figure 2:
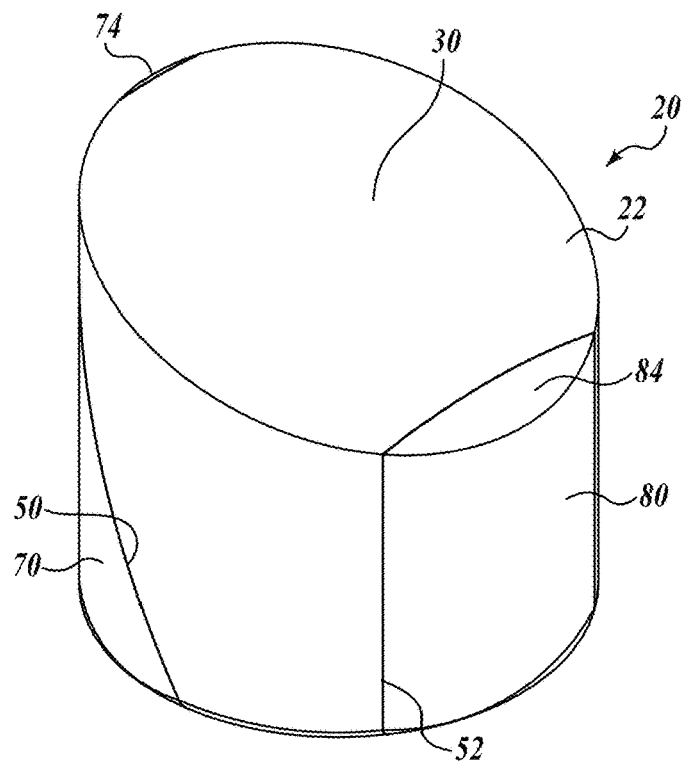
FIG. 2 is a top isometric view of the contact lens assembly of FIG. 1.
Figure 3:
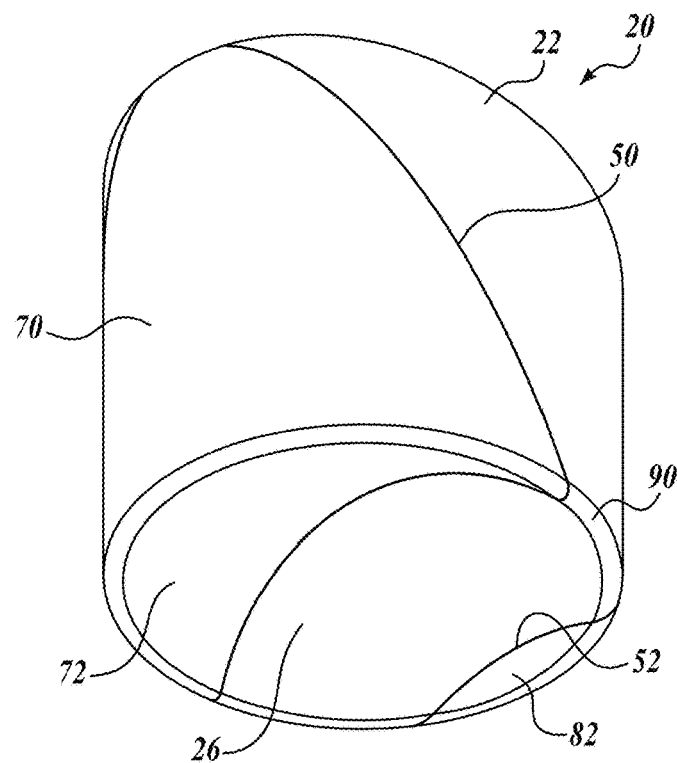
FIG. 3 is a bottom isometric view of the contact lens assembly of FIG. 1.
Figure 4:
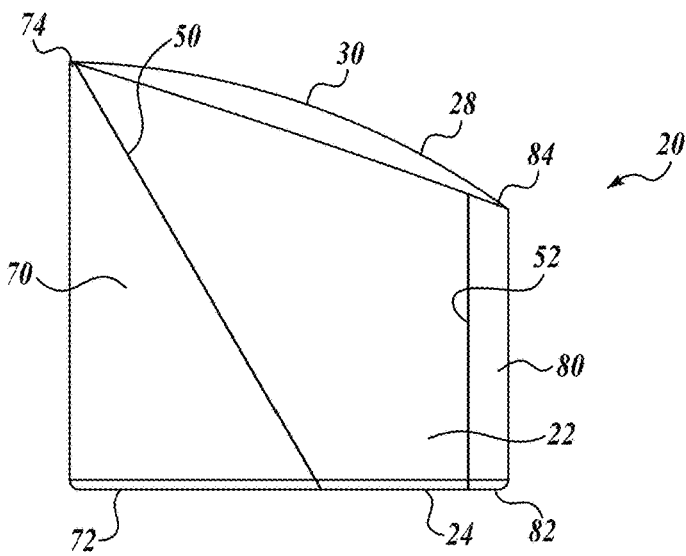
FIGS. 4-6 are various side views of the contact lens assembly of FIG. 1.
Figure 5:
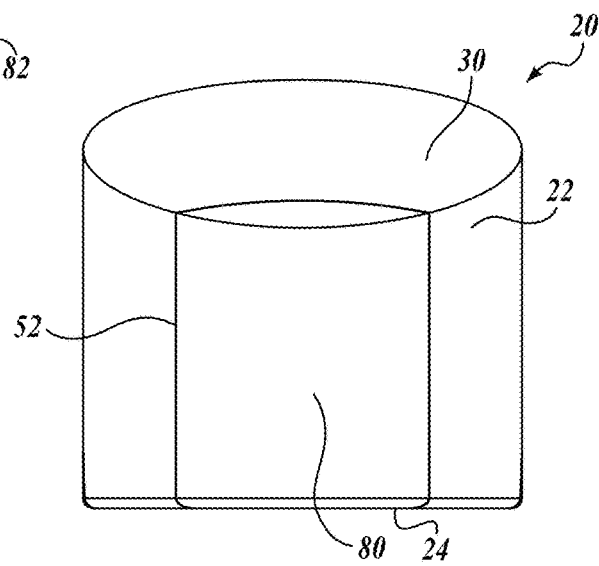
Figure 6:
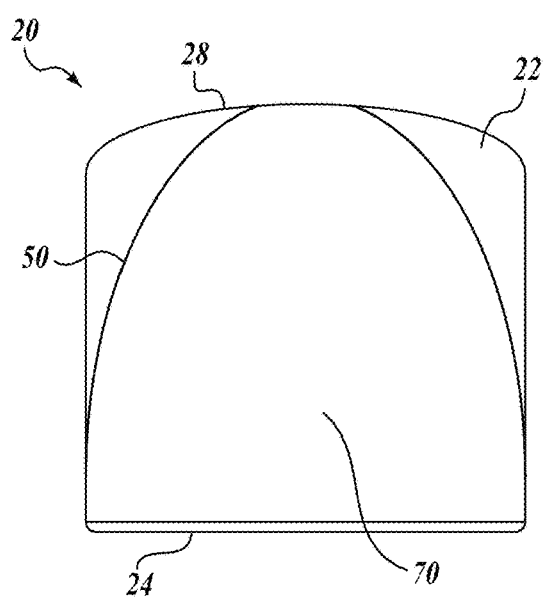
Figure 7:
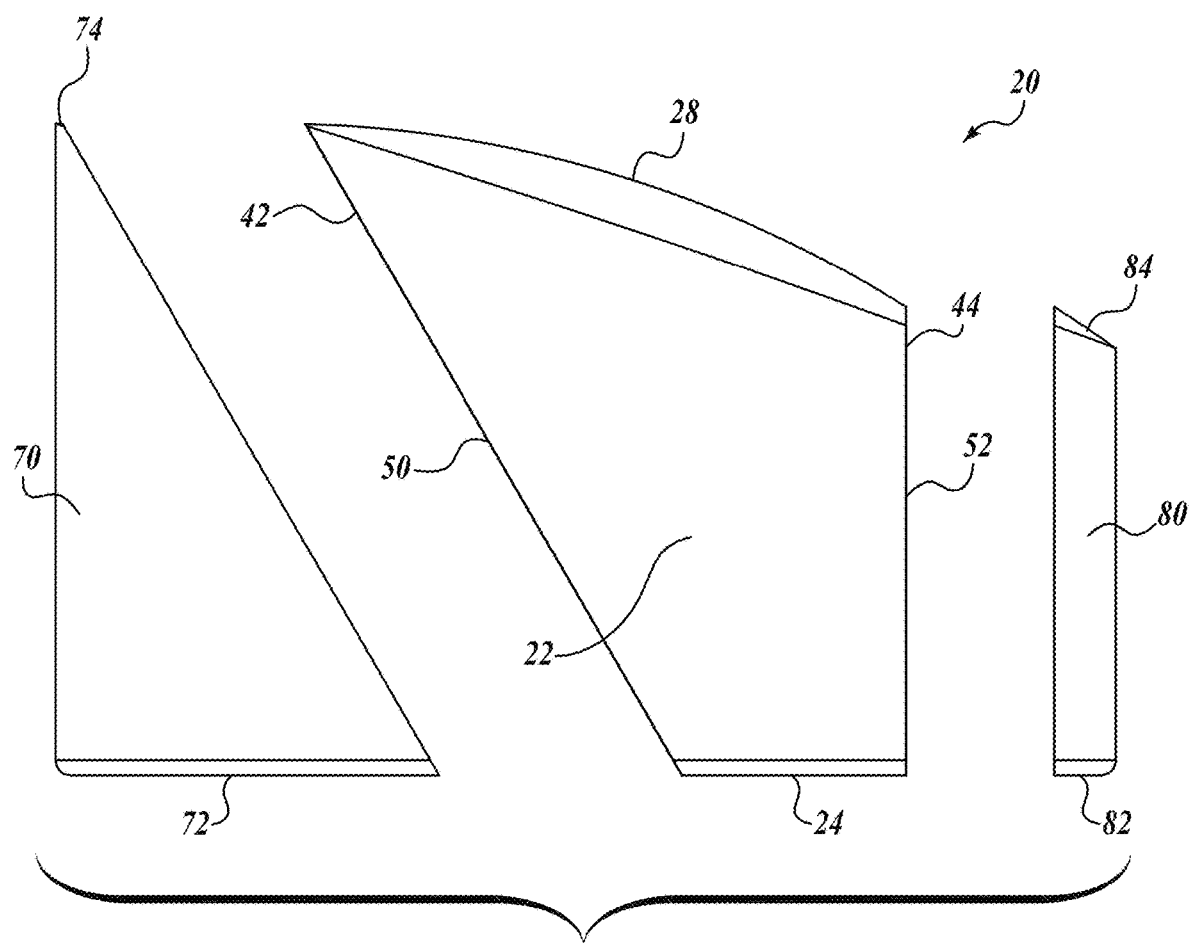
FIG. 7 is an exploded view of the contact lens assembly of FIG. 1.

In use, referring to FIG. 1, the lens assembly 20 is placed upon the eye E of a patient. To view the anterior chamber angle A of the eye E using the contact lens assembly 20 of the present disclosure, the viewer views in a direction along or substantially parallel or slightly angled relative to the optical axis 40 of the eye E, for example, along exemplary viewing paths P1, P2, or P2.

If surgically operating on the eye, surgical instruments may be inserted at the junction between the cornea C and sclera S regions of the eye E. The small sizing of the lens assembly 20 and the beveled edge 90 at the contact end 24 of the lens assembly 20 provide for areas for surgical instruments to be inserted into the eye E.

The user may need to view and/or surgically operate on multiple regions around the perimeter of the anterior chamber angle A of the eye. Therefore, the user may need to rotate the lens assembly 20 on the user's eye. In one embodiment of the present disclosure, the user may hold the lens assembly 20 by hand and rotate the lens assembly 20. In another embodiment of the present disclosure, the user may dispose the lens assembly 20 in a handle assembly 92, and rotate the handle to rotate the lens assembly 20. In another embodiment of the present disclosure, the lens assembly 20 may be rotatable within a collar attached to the handle. Therefore, the user would hold the handle in one position with one hand and use the second handle to rotate the lens assembly 20 within the collar.

In another embodiment of the present disclosure, the handle assembly may be configured for rotating the lens assembly 20 relative to the eye E. In one exemplary embodiment, the use can rotate the lens assembly 20 on the eye E by using a one-handed operation. In that regard, the user holds the handle assembly holding the lens assembly 20 steady against the patient's eye E. Then, the user moves a user-manipulatable actuator that affects rotational movement of the lens assembly 20 with respect to the handle assembly. An exemplary handle assembly designed for one-handed operation is described in greater detail below.

In other embodiments of the present disclosure, the lens handle may be a disposable or reusable lens handle. In some embodiments, the lens handle may be permanently affixed to the lens assembly. In one embodiment, the lens handle and the lens assembly are permanently affixed to one another and made for one-time use.

A method of making the lens assembly will now be described in greater detail. First, the maker manufactures a lens body 22 in accordance with embodiments of the present disclosure. The lens body 22 has been designed to have a contact end 24 defining at least a portion of an eye contact surface 26 of the lens assembly 20 and a viewing end 28 defining at least a portion of a viewing surface 30 of the lens assembly 20. The lens body 22 is a prism having an optical axis 40, a first planar surface 42 and a second planar surface 44, and magnification in the range of about 1.1× to about 1.5×.

The maker of the lens assembly 20 attaches first and second reflecting surfaces 50 and 52 to the first and second planar surfaces 42 and 44 of the lens body 22 in an opposing relationship to one another. Such reflecting surfaces may be plated on the lens body 22 using conventional plating techniques.

The maker of the lens assembly 20 then attaches a first outer portion 70 to the first reflective surface 50 and a second outer portion 80 to the second reflective surface 52. Such first and second outer portions 70 and 80 may be attached using adhesives designed to withstand high temperature sterilization techniques for reusable lens assemblies and without requiring a protective outer coating on the lens assembly 20.

The lens assembly 20 is then ground and polished to have desired ocular properties and a substantially circular cross-section through a plane perpendicular to the optical axis 40.

Referring now to FIGS. 8-14, another embodiment of the present disclosure will be described. The lens assembly 120 of FIGS. 8-14 is substantially similar to the lens assembly 20 of FIGS. 1-7, except for differences regarding the shape and dimensions of the lens assembly and the contact surface and the configuration of the reflecting surfaces relative to the lens body. Like elements in the lens 120 of FIGS. 8-14 use like numerals as the lens assembly 20 in FIGS. 1-7, except enumerated in the 100 series.

The contact lens 120 shown in the illustrated embodiment of FIGS. 8-14, like the embodiment of FIGS. 1-7, may be useful in glaucoma examination and/or surgical procedures.

As described above, surgical tools may be inserted into the eye E at the junction between the cornea C and sclera S regions of the eye E.

In the illustrated lens assembly 120 of FIGS. 8-14, the viewing surface 130 and the contact area of the eye contact surface 126 are larger than those surfaces of the previously described embodiment. In that regard, the lens body 122 is larger, providing a wider field of view, as compared to the lens body 22 of the illustrated embodiment of FIGS. 1-7. The larger lens body 122 has the advantageous effect of not having to be rotated as frequently for the user to view the portions or the entirety of the perimeter of the anterior chamber angle A.

In one embodiment, the contact surface 126 diameter of the lens assembly 120 is larger than the contact surface 26 diameter of the previously described embodiment of FIGS. 1-7. To enable use of a larger lens body 122 having a larger contact surface 126 diameter, the lens assembly 120 includes a cutout portion 134 in the contact end 124 to enable the insertion of surgical instruments, as can be seen FIGS. 8, 10, 12, and 14.

Like the previously described embodiment, the lens body 122 of FIGS. 8-14 has two planar surfaces 142 and 144 (see FIG. 14) that are configured as reflecting surfaces 150 and 152 (see FIG. 8) to define an unreversed prism gonioscopy contact lens assembly 120. The first reflecting surface 150 is disposed adjacent the lens body 122. In the illustrated embodiment, the first reflecting surface 150 is substantially planar and intersects only the viewing end 128 of the lens body 122. In that regard, the first reflecting surface 150 is truncated at corner 154 and includes shelf 172. This truncated configuration for the first reflecting surface 150 may help in reducing glare for the user of the lens assembly 120. This truncated configuration may also increase the field of the anterior chamber angle A in the anterior direction and increase the central view (straight down through the lens body 122 without using a mirror) to show an instrument moving from the point of incision I to the anterior chamber angle A.

The second reflecting surface 152 is disposed adjacent the lens body 122 opposing the first reflecting surface 150. The second reflecting surface 152 is substantially planar and extends between both the contact and viewing ends 124 and 128 of the lens body 122. The reflecting surfaces 150 and 152 may suitably be mirrored or TIR surfaces, or other reflecting surfaces.

In the illustrated embodiment, the first reflecting surface 150 is positioned at an angle of about 30 degrees relative to the optical axis 140 and intersects the optical axis 140 near the eye contact surface 126. The second reflecting surface 152 is positioned substantially parallel to the optical axis 140. In this configuration, the viewer looking in view path parallel to the optical axis 140 of the eye E, views the anterior chamber angle A of the eye E along path P3. Likewise, the viewer may also view the anterior chamber angle A of the eye E from a tilted view along path P4.

Figure 8:
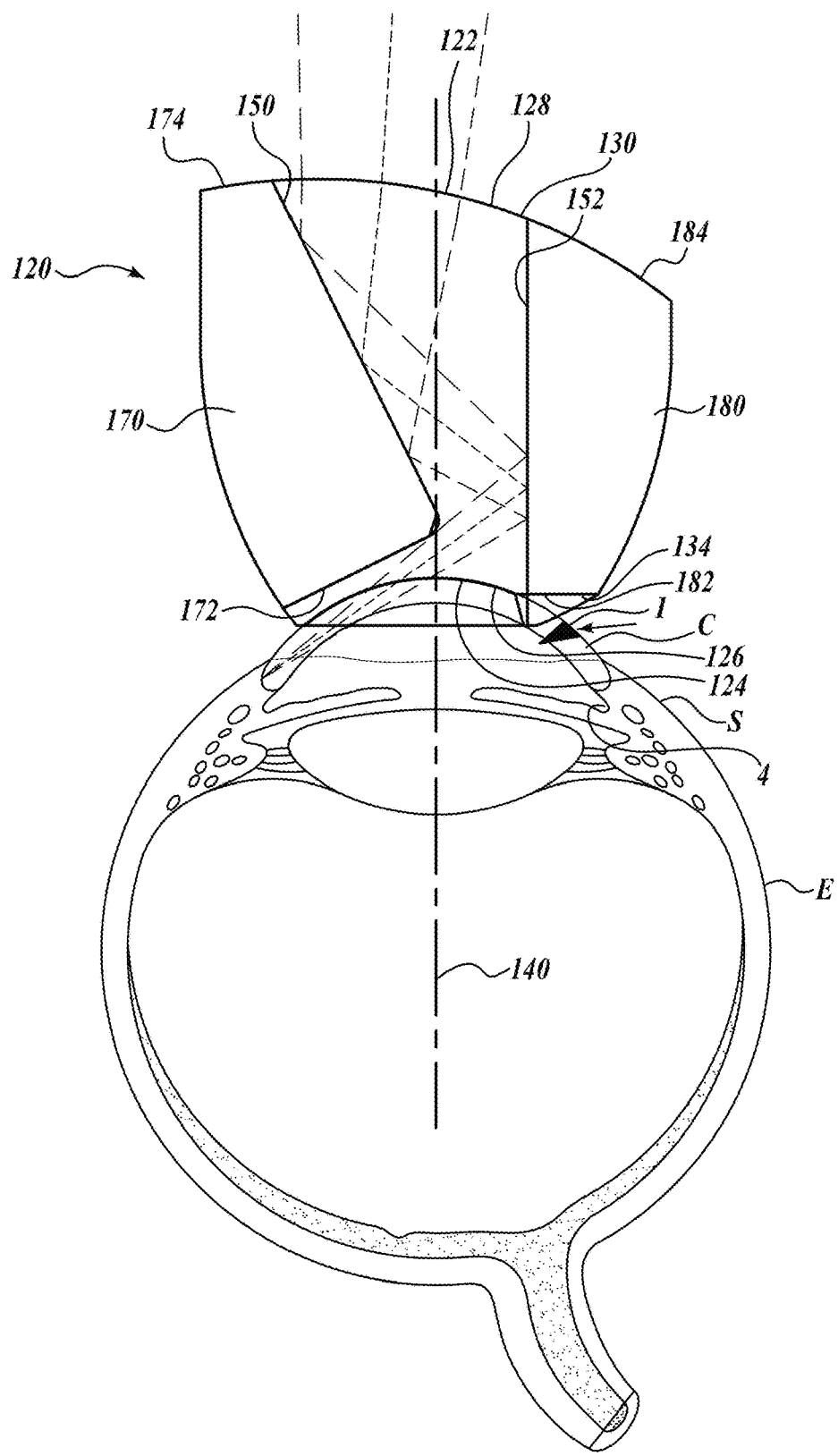
FIG. 8 is a side cross-sectional view of a contact lens assembly in contact with an eye in accordance with another embodiment of the present disclosure.
Figure 9:
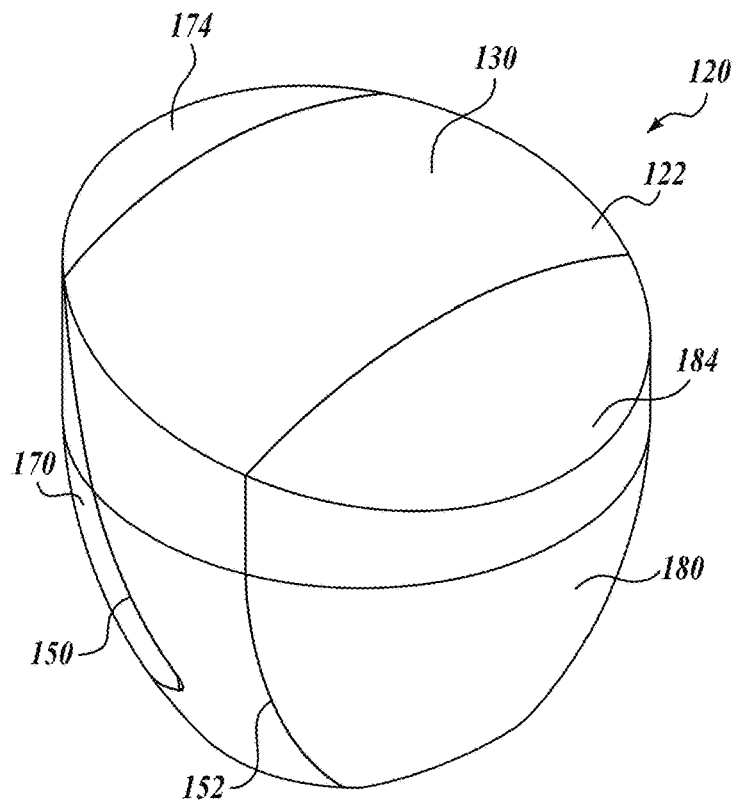
FIG. 9 is a top isometric view of the contact lens assembly of FIG. 8.
Figure 10:
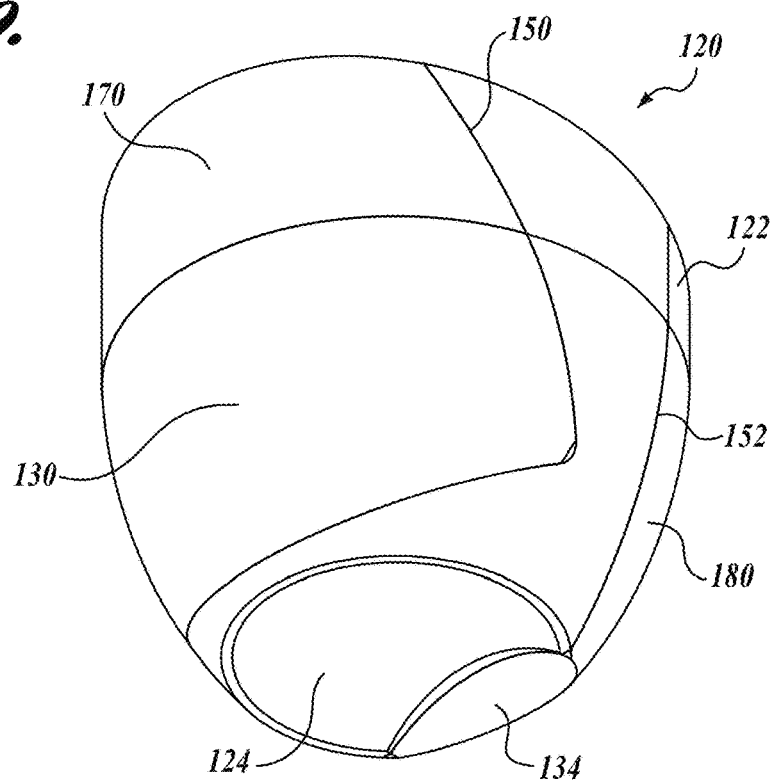
FIG. 10 is a bottom isometric view of the contact lens assembly of FIG. 8.
Figure 11:
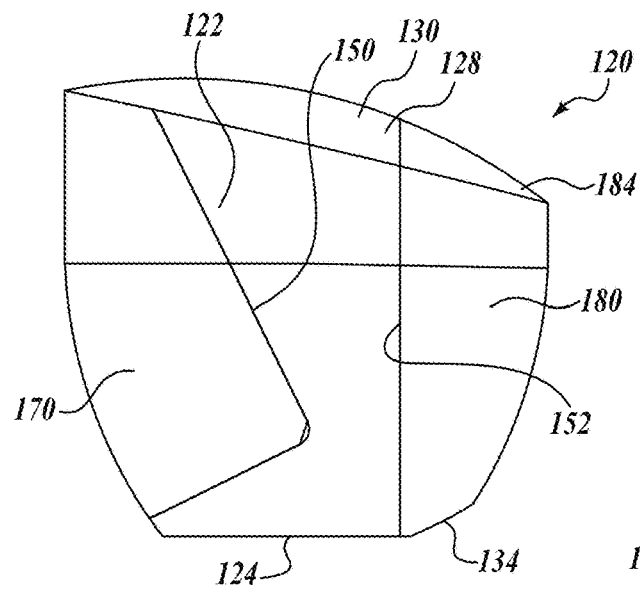
FIGS. 11-13 are various side views of the contact lens assembly of FIG. 8.
Figure 12:
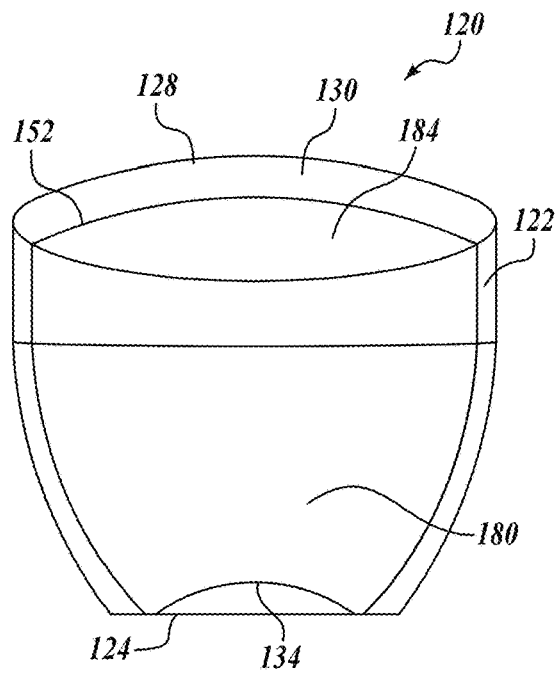
Figure 13:
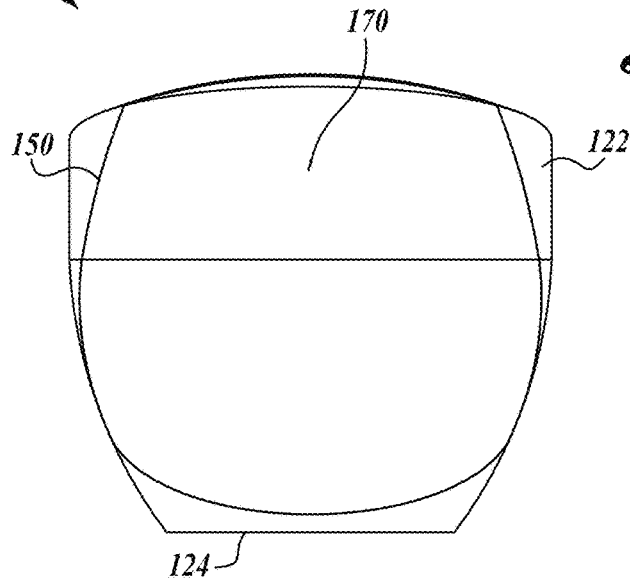
Figure 14:
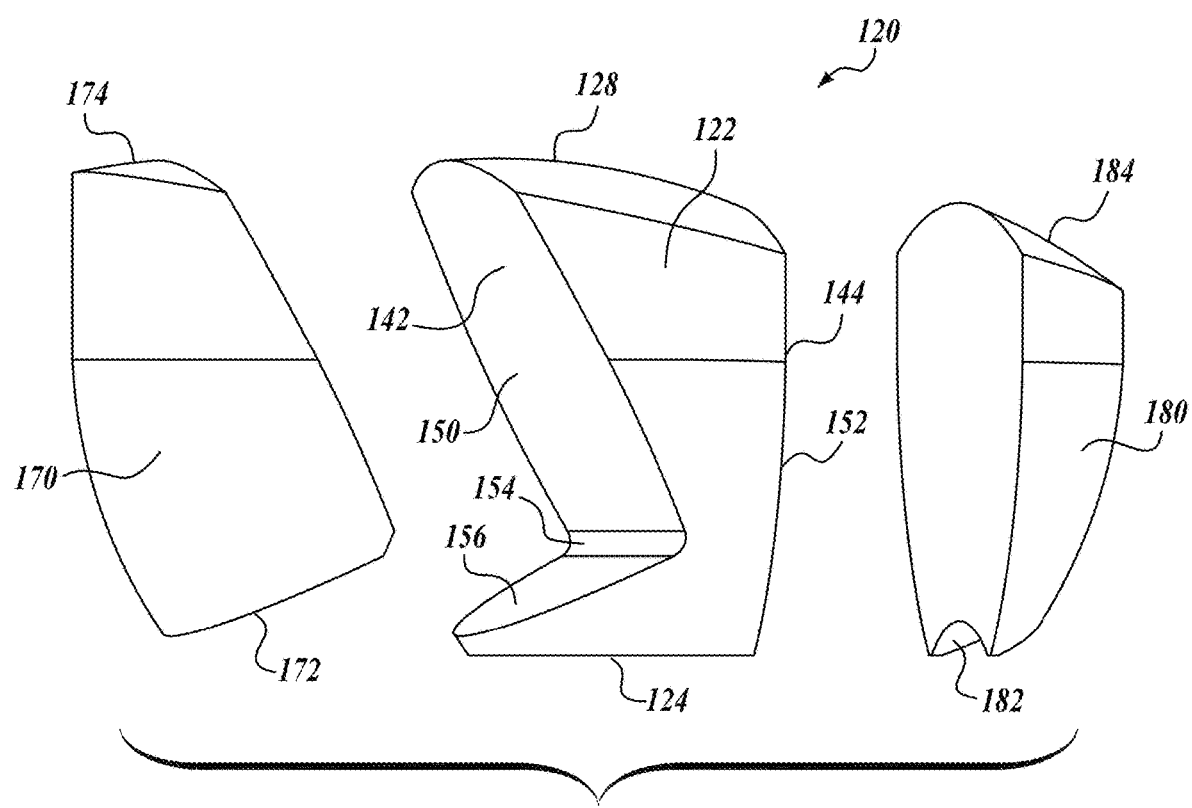
FIG. 14 is an exploded view of the contact lens assembly of FIG. 8.

In use, referring to FIG. 8, the lens assembly 120 is placed upon the eye E of a patient against the eye. To view the periphery of the anterior chamber angle A of the eye E using the contact lens assembly 120 of the present disclosure, the viewer views in a direction along or substantially parallel or slightly titled relative to the optical axis 140 of the of the lens assembly 120, for example, along exemplary viewing paths P4, P5, or P6.

If surgically operating on the eye, surgical instruments may be inserted at the junction between the cornea C and sclera S regions of the eye E. The cutout region 134 at the contact end 124 of the lens assembly 120 provides an area for surgical instruments to be inserted into the eye E.

A method of making the lens assembly will now be described in greater detail. First, the maker manufactures a lens body 122 in accordance with embodiments of the present disclosure. The maker of the lens assembly 120 attaches first and second reflecting surfaces 150 and 152 to the first and second planar surfaces 142 and 144 of the lens body 122 in an opposing relationship to one another. Such reflecting surfaces may be plated on the lens body 122 using plating techniques.

The maker of the lens assembly 120 then attaches a first outer portion 170 to the first reflective surface 150 and a second outer portion 180 to the second reflective surface 152. Such first and second outer portions 170 and 180 may be attached using adhesives designed to withstand high temperature cleaning techniques for lens assemblies and without requiring a protective outer coating on the lens assembly 20.

The lens assembly 120 is then ground and polished to have desired ocular properties and a substantially circular cross-section through a plane perpendicular to the optical axis 140.

Figure 21:
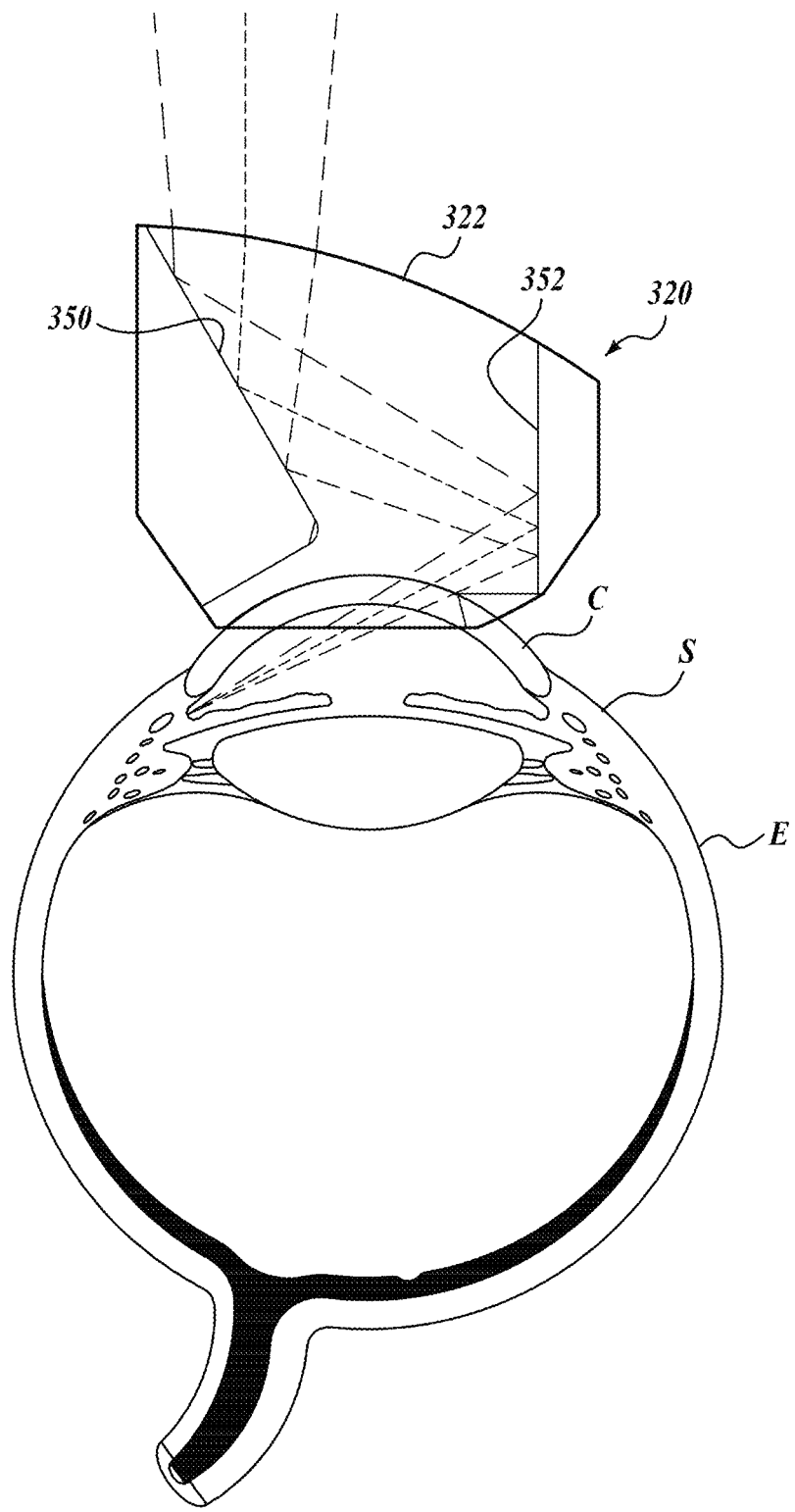
FIGS. 21-23 are views of a contact lens assembly in accordance with another embodiment of the present disclosure, with the contact lens assembly having a wider field of view as compared to the embodiment shown in FIG. 8.
Figure 22:
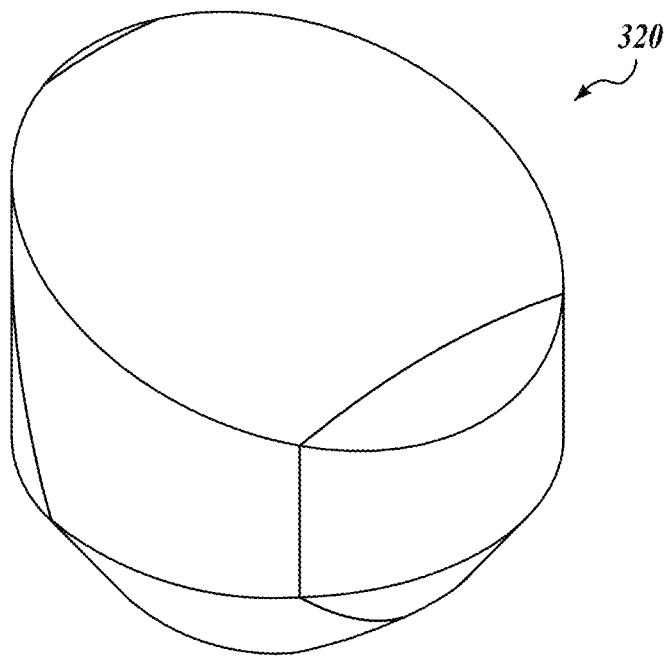
Figure 23:
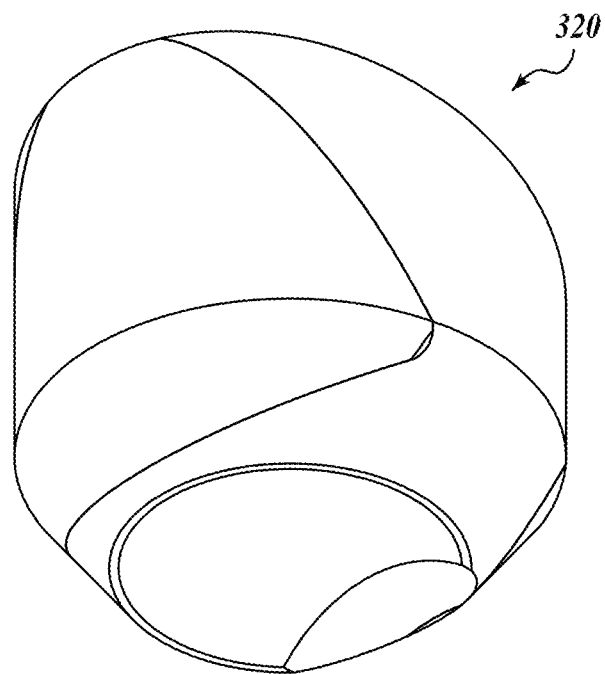

Referring now to FIGS. 21-23, another embodiment of a contact lens assembly is provided. The embodiment of FIGS. 21-23 is substantially similar to the embodiment of FIGS. 8-14 in design and manufacture, except that reflecting surfaces 350 and 352 are moved outbound to provide a wider central view (straight down through the lens body 322 without using a mirror) to provide an enhanced view of an instrument moving from the point of incision I to the anterior chamber angle A.

Embodiments of handle assemblies for one-handed operation will now be described in greater detail with reference to FIGS. 24A-36. Such handle assemblies can be used in combination with the lenses described above.

Figure 24A:
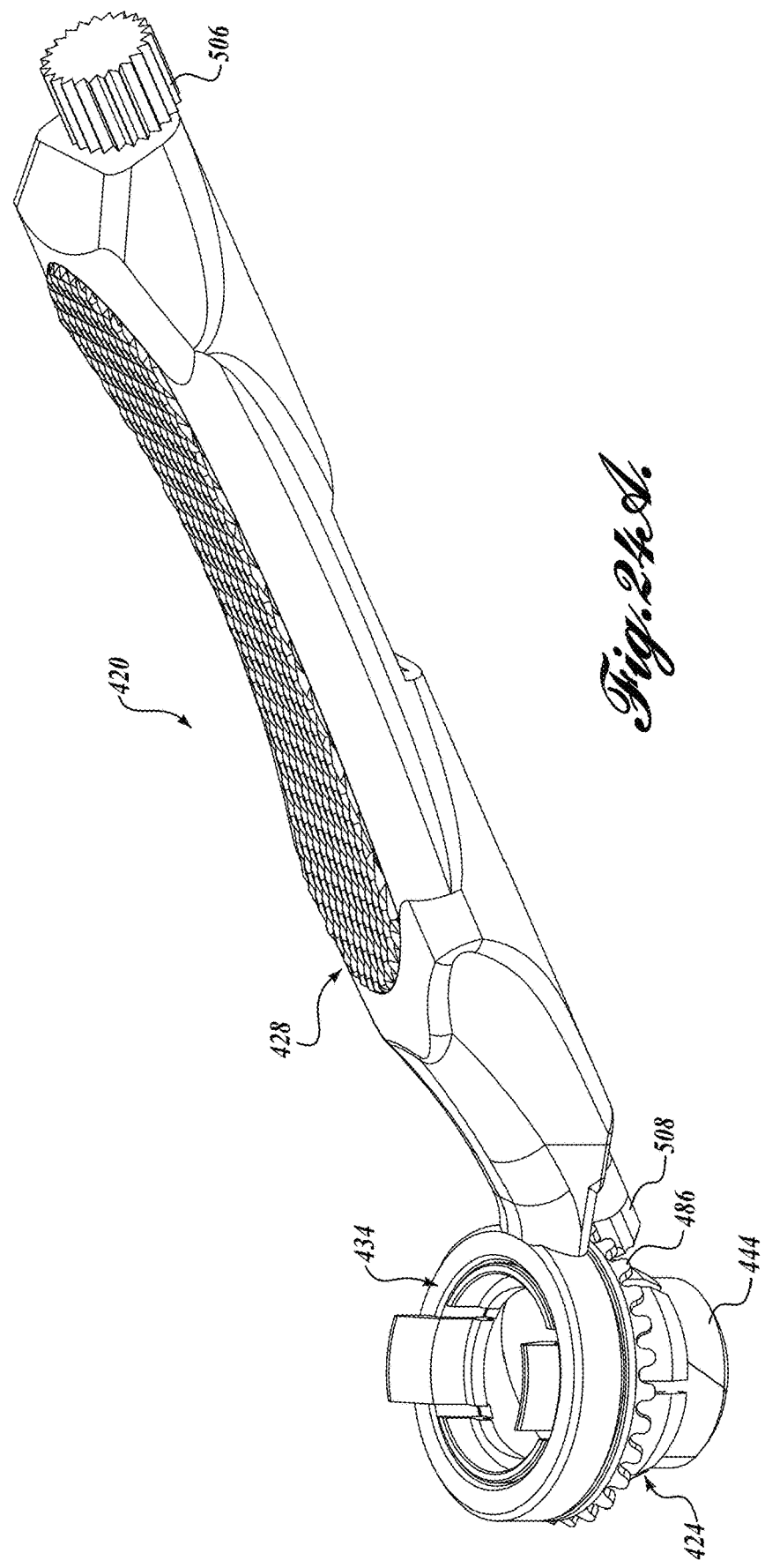
Figure 24B:
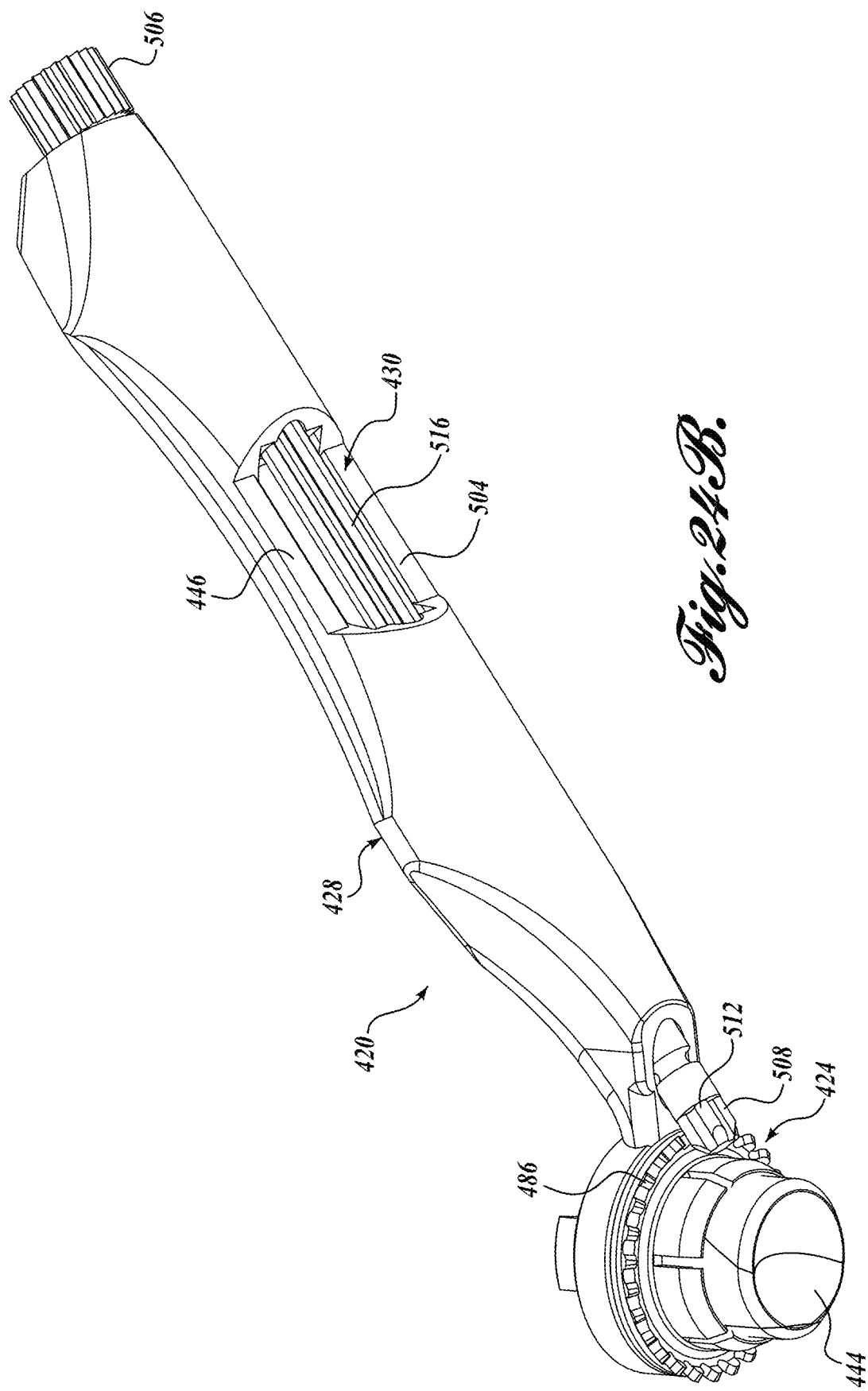

Turning now to FIGS. 24A-24B, there is shown one example of a lens handle, generally designated 420, formed in accordance with aspects of the present disclosure. The lens handle 420 is suitable for use during medical procedures of the eye, such as for example, the treatment of glaucoma or the like. Generally described, the lens handle 420 includes a lens assembly 424 carried by or otherwise associated with a handle 428. As will be described in more detail below, the lens handle 420 is configured for one-handed operation, including a user manipulatable actuator 430 (see FIG. 24B) that affects movement of the lens assembly 424 with respect to the handle 428. In use, the lens handle 420 can be grasped with one hand of the user while the other hand of the user is free to hold another instrument associated with the particular medical procedure. While the lens handle 420 is in the hand of the user, the lens assembly 424 can be manipulated firstly by movement of the handle 428 via the user's wrist or arm, and secondly, by actuation of the actuator 430 with the user's finger or fingers of the hand grasping the handle 428.

Referring to FIGS. 24A-30, the components of the lens handle 420 will be described in more detail. As shown in FIGS. 24A, 24B, 25, and 30, the lens assembly 424 is carried at the end of the handle 428. In that regard, the handle 428 includes an elongate body 432 to which a lens assembly retainer 434 is formed, attached, or otherwise provided at the distal end thereof. In the embodiment shown in FIGS. 24A and 30, the lens assembly retainer 434 is in the form of a ring defining a cylindrical bore 436 (FIG. 30), and having walls 438 with a generally rectangular cross section and a top chamfered edge. The lens assembly retainer 434 is disposed at an angle α with respect to the longitudinal axis of the handle 428, as shown in FIG. 30. In some embodiments, the angle α is approximately between 30 and 40 degrees or greater, and in one embodiment, is approximately 35 degrees. In other embodiments, the angle α is approximately between 0-15 degrees or greater for use with, for example, slit lamp lenses. As such, one or more embodiments may employ an angle α approximately between 0-50 degrees. As will be described in more detail below, the lens assembly retainer 434 is sized and configured to interface with the lens assembly 424 for releasable securement therewith. Once coupled, the lens assembly 424 is allowed to rotate about the axis 440 of the bore 436.

Referring now to FIG. 25, the lens assembly 424 in some embodiments includes a collar-like lens housing 442 ("lens housing 442") that surrounds a lens 444. The lens 444 can be any suitable "on-axis" style viewing lens (e.g., an unreversed viewing lens described above).

Figure 26:
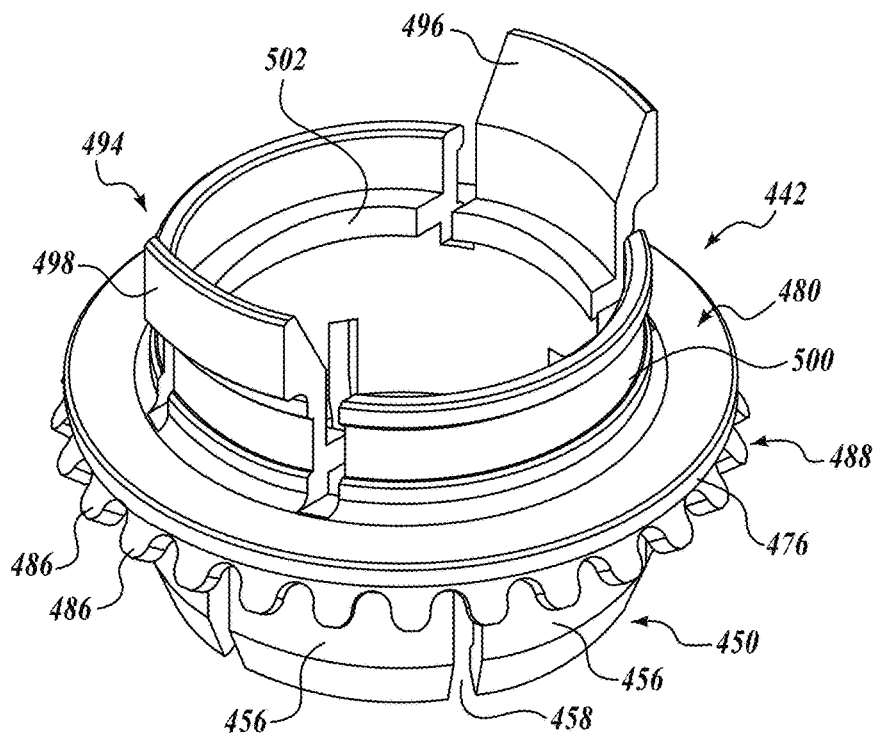
Figure 27:
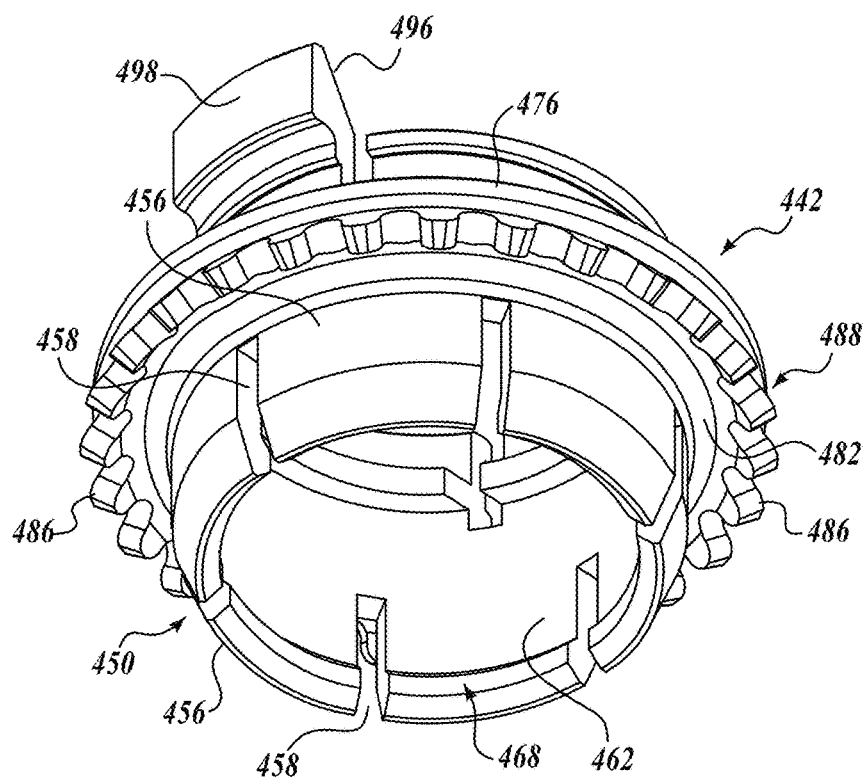
Figure 28:
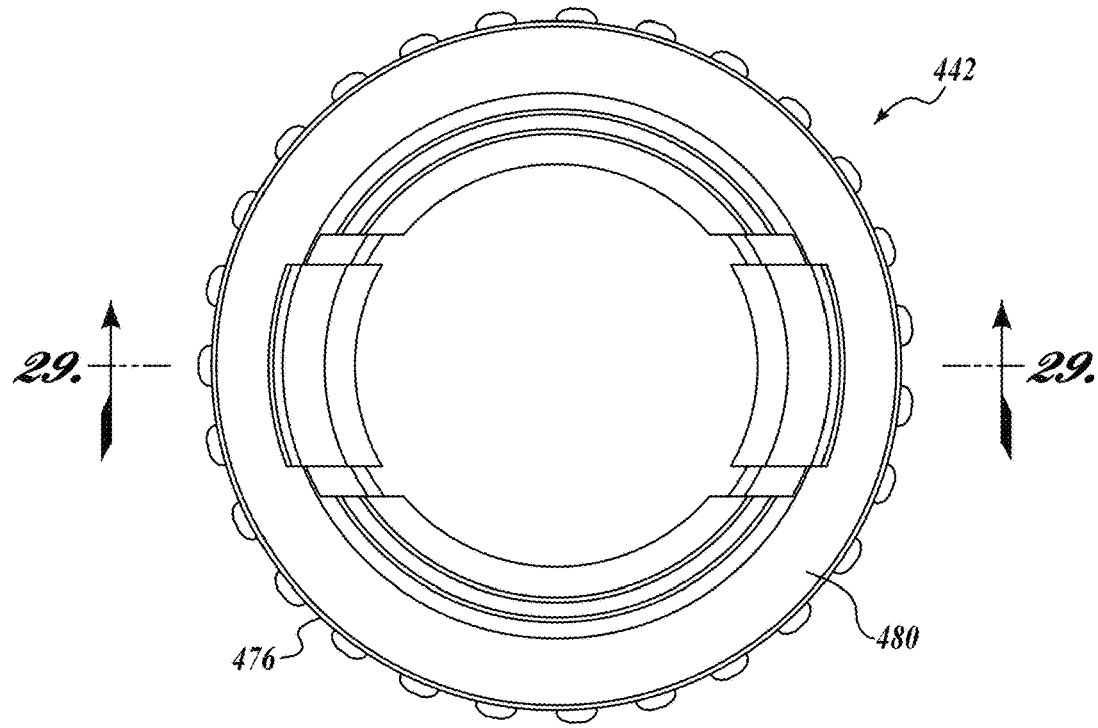
Figure 29:
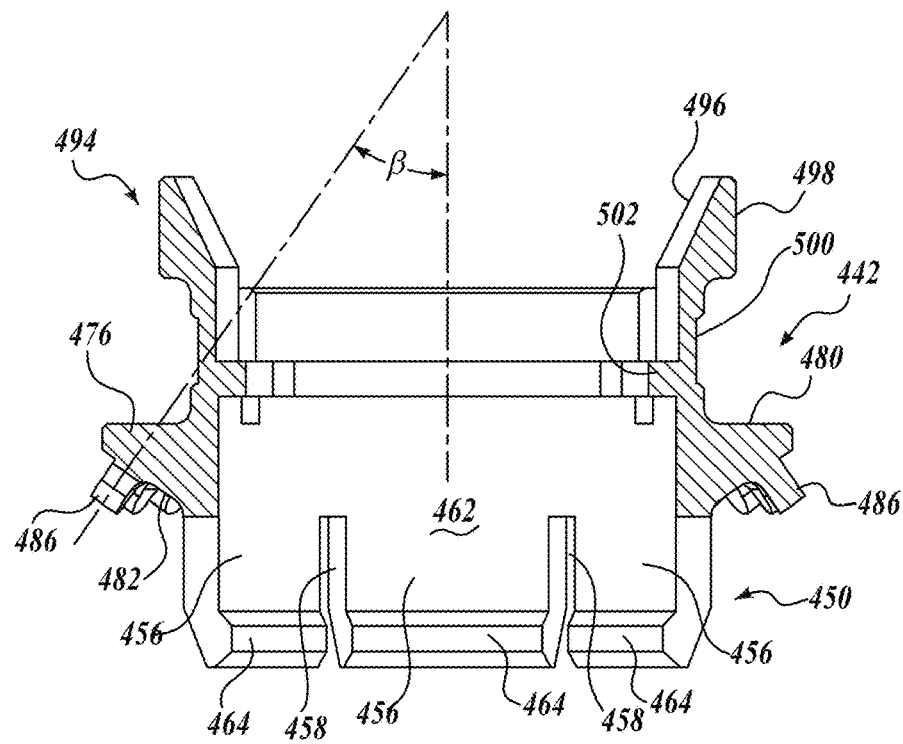
Figure 33:
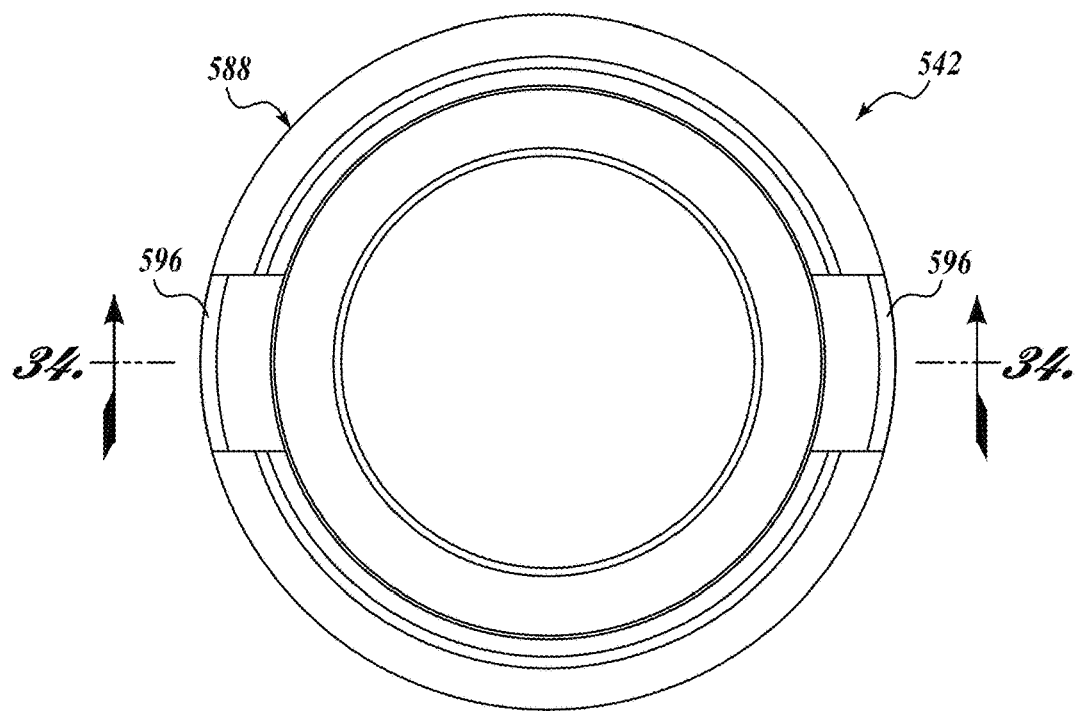

At its distal end, the lens housing 442 includes a lens retaining interface 450 configured to retain or hold the lens 444 in position during use. In some embodiments, the lens retaining interface 450 is in the form of a collet having a plurality of annularly disposed legs 456 separated by kerfs or slots 458, as shown in FIGS. 26, 27, and 29. The collet defines a generally cylindrical, inner cavity 462 for receiving at least a portion of the lens 444 therein. As shown in FIG. 29, the outer, free ends of the legs 456 can be slanted generally inwardly in some embodiments, each forming an engagement flange segment 464. Together, the engagement flange segments 464 define the distal opening 468 (see FIG. 27) of the lens housing 442, which communicates with the inner cavity 462.

In some embodiments, the legs 456 are configured and arranged to slightly flex outwardly during installation of the lens 444. As a result, the engagement flange segments 464 of the slightly flexed legs 456 apply pressure to the outer surface of the lens 444. This pressure, along with frictional forces between the lens 444 and the inner walls of the housing 442, releasably retain or hold the lens 444. In the embodiment shown in FIGS. 24A and 24B, a portion of the lens 444 extends outwardly of the distal end of the lens housing 442 once retained by the collet of the lens housing 442. It will be appreciated that the lens 444 can be any type of lens useful in one or more surgical procedures, including but not limited to a direct viewing lens, a mirrored lens, an unreversed viewing lens, etc.

Returning to FIGS. 26, 27, and 29, the lens housing 442 also includes an annular flange 476 spaced proximally of the lens retaining interface 450 (e.g., collet, etc.). The annular flange 476 extends radially outwardly of the housing 442, and in some embodiments, has a somewhat truncated, right triangular-like cross section (FIG. 29). In that regard, the flange 476 defines a proximal facing surface 480 positioned orthogonal to the longitudinal axis of the housing 442 and a slanted surface 482. Extending from the slanted surface 482 of the flange 476 are a plural of gear teeth 486, thereby forming a ring gear 488 (see FIGS. 26 and 27). In the embodiment shown, the ends of the teeth 486 of the ring gear 488 are generally rounded and extend at an angle β with respect to the longitudinal axis of the housing 442 (see FIG. 29). In some embodiments, the angle β is approximately between 30-40 degrees, and in one embodiment, is approximately 35 degrees. In these and other embodiments, the angle β is approximately equal to the angle α.

The lens housing 442 further includes a handle coupling interface 494 disposed at its proximal end, opposite the lens retaining interface 450. The handle coupling interface 494 is configured to couple the lens housing 442 with the lens assembly retainer 434 of the handle 428. In some embodiments, the handle coupling interface 494 is configured to releasably couple the lens housing 442 to the handle 428.

In the embodiment shown in FIGS. 26, 27, and 29, the handle coupling interface 494 includes a pair of opposing snap retainers 496 extending in the proximal direction from the outer annular walls of a proximal section of the lens housing 442. The snap retainers 496 include radially outwardly extending flange sections 498, the bottoms of which form an annular channel 500 with the proximal facing surface 480 of the annular ring 476. The snap extensions 496 are configured and arranged to slightly flex inwardly during coupling of the lens assembly 424 to the handle 428. In that regard, the flange segments 498 snap back (with the snap extensions) after they pass through the bore 436 of the lens assembly retainer 434, causing the lens assembly retainer 434 to be disposed in the channel 500 and surrounding the lens housing 442, and thus, coupling the lens assembly 424 to the handle 428. Once coupled, the lens assembly 424 is allowed to rotate with respect to the handle 428 about the longitudinal axis 440 of the bore 436. In use, the longitudinal axis 440 is generally aligned with the optical axis of the patient's eye.

In some embodiments, the lens housing 442 includes an optional, inner annular flange 502 positioned somewhat in the proximal cavity. The inner annular flange 502 in some embodiments may be used as an end stop for insertion of the lens 444.

Returning now to FIGS. 24A, 24B, and 30, the actuator 430 is carried by the body 432, and is configured and arranged to interface with the lens assembly 424 in order to manipulate the lens assembly 424. In the embodiment shown in FIG. 30, the actuator 430 includes a drive shaft 504 journaled for rotation about an axis parallel with the longitudinal axis of the handle 428. At the distal end of the drive shaft 504 there is formed, attached or otherwise provided a drive gear 508. The drive gear 508 includes a plurality of teeth 512 configured and arranged to cooperate with the teeth 486 of the ring gear 488 such that rotation of the drive shaft 504 results in rotation of the lens assembly 424. Along the length of the body, the drive shaft 504 can include a lever in the form of a knob or can be formed with a splined or knurled section to interface with a finger or fingers of the user. In that regard, the handle body 432 may include a recess 446 or the like to provide access to the drive shaft 504 in order for the user's finger to contact and rotate the drive shaft 504. Access to the drive shaft 504 is positioned in an ergonomic location such that the user (e.g., surgeon) can hold the handle 428 and rotate the drive shaft in a one handed operation. The handle body 432 in some embodiments may be ergonomically configured for comfort when gripped by the doctor and can include one or more knurled surface sections.

Additionally or alternatively, the drive shaft 504 may include an enlarged knob 506 formed, affixed, mounted, or otherwise disposed at the proximal end thereof. In several embodiments of the present disclosure, the knob 506 provides an alternative or additional lever suitable for use by the doctor in order to rotate the drive shaft 504.

FIGS. 31A and 31B illustrate another embodiment of a lens handle 520 in accordance with aspects of the present disclosure. The lens handle 520 is substantially identical to lens handle 420 described above with reference to FIGS. 24A-30 except for the differences that will now be described. In that regard, attention is directed to FIGS. 31A-36, which illustrates one example of a lens handle 520 in which the actuator 530 is driven by a drive motor 552. As best shown in FIGS. 31B and 32, the drive motor 552 is mounted to the proximal end of the handle body 532 via mounting bracket 554 or other suitable structure. The drive motor 552 includes an output shaft 590 that is configured to interface (e.g., keyed, splined, pinned, etc.) with the knob 606 of the drive shaft 604 for effecting co-rotation therebetween. While the output shaft 590 is oriented coaxially with the drive shaft 604, other configurations are possible. For example, in some embodiments, the output shaft 590 can be offset with the drive shaft 604 or can be disposed orthogonal thereto, etc.

Drive signals for operating the drive motor 552 with either continuous or incremental rotation can be supplied via activation of a switch 594. The switch 594 can be mounted on the handle 528 or remote therefrom, such as a foot switch, table mounted switch, etc. As such, activation of the switch 594, such as by movement, delivers device specific control signals to be carried out by the drive motor 552. In some embodiments, the drive motor 552 can include but is not limited to AC or DC electric motor, a stepper motor, a servo motor, etc.

In one embodiment, the drive motor 552 includes a stepper motor that receives signal pulses from a controller 596, such as a microcontroller, via operation of the switch 594. The stepper motor can be servo-controlled, depending on its intended application. In response to the signal pulses, the stepper motor rotates the output shaft 590 clockwise/counterclockwise, in increments or "steps" of full shaft rotation. In turn, the output shaft 590 drives the drive shaft 204 in order to rotate the lens assembly 524 from 0-90 degrees in some embodiments (e.g., using a 4-mirrored lens, etc.), and between 0-360 degrees in other embodiments.

The lens handle 520 also employs another example of a lens housing, generally designated 542. The lens housing 542 can also be employed with the handle 28 described above. In that regard, various configurations of the lens housing may be employed with the lens handles 420, 520 depending on its intended application (e.g., which lens is preferred by the doctor for a given ophthalmological procedure). In that regard, any lens housing that either permanently or selectively retains a lens while also providing a suitable interface with the actuator may be practiced with embodiments of the present disclosure.

Figure 34:
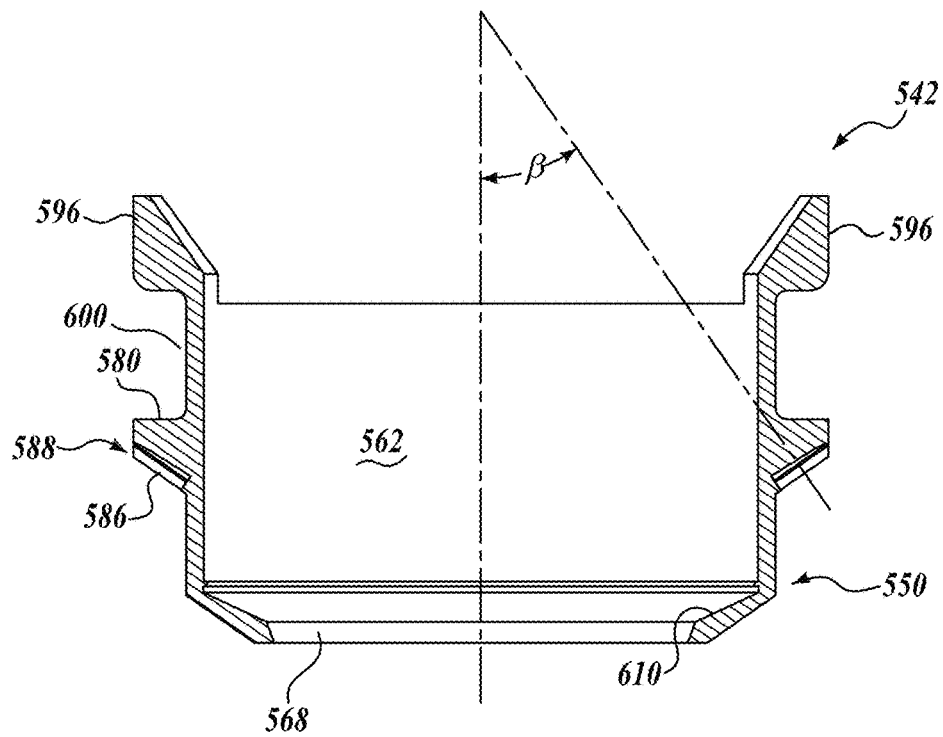
Figure 35:
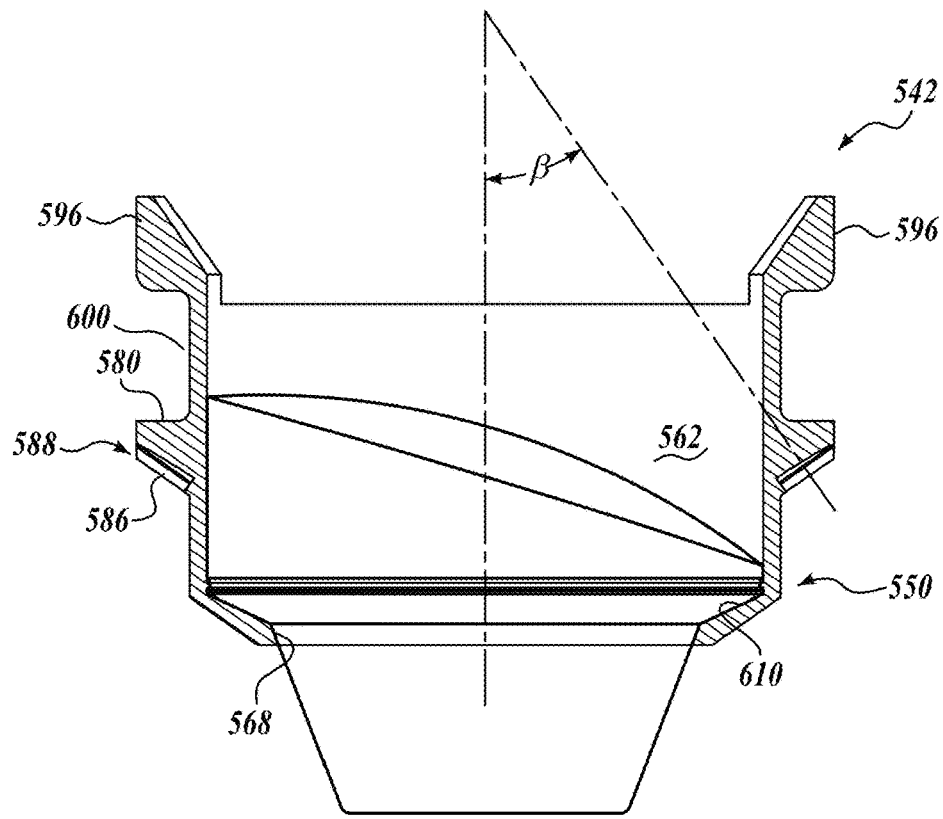
Figure 36:
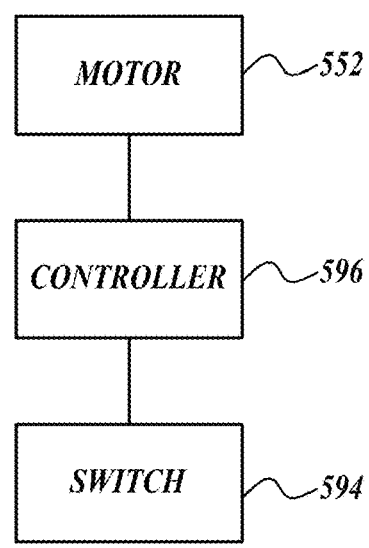

As shown in FIGS. 34-36, the lens housing 542 is configured for use with, for example, a prism lens 544 (see FIG. 34). In that regard, the lens housing 542 is generally collar shaped for retaining the lens 544. The lens housing 542 includes a handle coupling interface 594 configured to couple the lens housing 542 to the lens assembly retainer 534 of the handle 528. In some embodiments, the handle coupling interface 594 is configured to releasably couple the lens housing 542 to the handle 528.

At its distal end, the lens housing 542 includes a lens retaining interface 550 configured to retain or hold the lens 544 in position during use. In some embodiments, the lens retaining interface 550 forms of an internal shoulder 610 formed by a distal opening 568 of smaller cross section than the interior cavity 562 of the main body of the lens housing 542. The shoulder 610 and opening 568 cooperatively receive the lens 544 when assembled, as shown in FIG. 35.

While one example of a gear arrangement has be illustrated and described, it will be appreciated that other rotary to rotary mechanisms may be employed in embodiments of the lens handle 420, 520. Additionally, other actuators that provide rotation to the lens assembly may be practiced with embodiments of the present disclosure. For example, actuators employing reciprocating to rotary mechanisms, etc., to rotate the lens assembly 424, 524 may be used.

It should be noted that for purposes of this disclosure, terminology such as "upper," "lower," "vertical," "horizontal," "fore," "aft," "inner," "outer," "inwardly," "outwardly," "proximal", "distal," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings.

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A double-reflecting contact lens for viewing the anterior chamber and the anterior chamber angle of an eye, the eye having an optical axis, the lens comprising:
    a lens body having a distal end defining at least a portion of a first surface for contacting an eye and a proximal end defining at least a portion of a second surface;
    a first reflecting surface disposed adjacent the lens body, wherein the first reflecting surface is a planar surface extending from the proximal end terminate at to a middle region in the lens body located between the proximal end and the distal end; and
    a second reflecting surface disposed adjacent the lens body, wherein the second reflecting surface is a planar surface extending from the proximal end to the distal end, the second reflecting surface opposing the first reflecting surface at an angle relative to the first reflecting surface;
    a planar shelf adjoining the first reflective surface, the planar shelf extending from an end of the first reflective surface that terminates in the middle region of the lens body to an outer surface of the lens body, wherein at least a portion of the lens body extends between the planar self and the distal end of the lens body, and wherein the outer surface is different from the distal end, proximal end, the first reflecting surface, and the second reflecting surface.

2. The lens of claim 1, wherein the second reflecting surface is parallel to the optical axis of the eye.

3. A double-reflecting contact lens comprising:
    a lens body having a distal end defining at least a portion of a first surface for contacting an eye and a proximal end defining at least a portion of a second surface;
    a first reflecting surface disposed adjacent the lens body and including a first planar reflecting portion and a planar shelf portion, wherein the first planar reflecting portion extends from a first end at the proximal end of the lens body to terminate at a second end in a middle region in the lens body between the proximal end and the distal end, the planar shelf portion adjoining the first planar reflecting portion and extending from the second end of the first planar reflecting portion to an outer surface of the lens body;
    a second reflecting surface disposed adjacent the lens body, wherein the second reflecting surface is a planar surface extending from the proximal end to the distal end, the second reflecting surface opposing the first planar reflecting surface at an angle relative to the first reflecting surface,
    wherein the planar shelf portion is perpendicular to the first planar reflecting portion.

4. The lens of claim 3, wherein the interface between the first planar reflecting portion and the planar shelf portion is truncated.

5. The lens of claim 3, further comprising a first outer portion of the lens adjacent the first reflecting surface and the planar shelf portion.

6. The lens of claim 5, wherein the first outer portion is defined by at least the first reflecting surface and an outer surface of the first outer portion.

7. The lens of claim 5, further comprising a second outer portion of the lens adjacent the second reflecting surface.

8. The lens of claim 7, wherein the second outer portion is defined by at least the second reflecting surface and an outer surface on the second outer portion.

9. The lens of claim 1, wherein the lens body is configured to provide a magnification in the range of between 1× to about 2×.

10. A method of viewing the anterior chamber and the anterior chamber angle of an eye, comprising:
    (a) placing a double-reflecting contact lens according to claim 1 on the eye of a patient;
    (b) holding the contact lens in a substantially constant position and viewing a first location in the anterior chamber of the eye of the patient; and
    (c) rotating the contact lens on the eye of the patient and viewing a second location in the anterior chamber of the eye of the patient.

11. The method of claim 10, wherein the lens body is configured to provide a magnification in the range of between 1× to about 2×.

\* \* \* \* \*